United States Patent
Hancock

(10) Patent No.: US 9,848,852 B2
(45) Date of Patent: *Dec. 26, 2017

(54) SYSTEM AND METHOD FOR FOCUSING ULTRASOUND IMAGE DATA

(71) Applicant: Volcano Corporation, San Diego, CA (US)

(72) Inventor: Andrew Hancock, Sacramento, CA (US)

(73) Assignee: Volcano Corporation, San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/133,072

(22) Filed: Apr. 19, 2016

(65) Prior Publication Data

US 2016/0302770 A1    Oct. 20, 2016

Related U.S. Application Data

(63) Continuation of application No. 13/974,757, filed on Aug. 23, 2013, now Pat. No. 9,314,226.

(Continued)

(51) Int. Cl.
*G03B 42/06*    (2006.01)
*A61B 8/08*    (2006.01)
(Continued)

(52) U.S. Cl.
CPC .......... *A61B 8/5207* (2013.01); *A61B 8/0891* (2013.01); *A61B 8/12* (2013.01);
(Continued)

(58) Field of Classification Search
CPC ....... A61B 8/5207; A61B 8/12; A61B 8/4488; G01S 7/52034; G01S 15/8927; G01S 15/8997
(Continued)

(56) References Cited

U.S. PATENT DOCUMENTS

| | | | | | |
|---|---|---|---|---|---|
| 4,633,882 | A | * | 1/1987 | Matsuo | A61B 1/0052 600/146 |
| 4,951,677 | A | * | 8/1990 | Crowley | A61B 5/6848 600/109 |

(Continued)

OTHER PUBLICATIONS

International Search Report and Written Opinion received in Patent Cooperation Treaty Application No. PCT/US2013/056405, dated Dec. 11, 2013, 27 pages.

(Continued)

*Primary Examiner* — Mark Hellner

(57) ABSTRACT

Sold-state intravascular ultrasound (IVUS) imaging devices, systems, and methods are provided. Some embodiments of the present disclosure are particularly directed to flexible and efficient systems for focusing IVUS echo data received from transducers including polymer piezoelectric micromachined ultrasound transducers (PMUTs). In one embodiment, an ultrasound processing system includes first and second aperture engines coupled to an engine controller, which provides aperture assignments to the first and second aperture engines. The aperture engines receive the assignment and a portion of A-line data, perform one or more focusing process on the received A-line data, and produce focused data in accordance with the aperture assignment. In some embodiments, once an aperture engine has produced focused data, the engine controller clears the aperture engine and assigns another aperture.

13 Claims, 25 Drawing Sheets

Related U.S. Application Data

(60) Provisional application No. 61/693,118, filed on Aug. 24, 2012.

(51) Int. Cl.
*A61B 8/12* (2006.01)
*A61B 8/00* (2006.01)
*G01S 15/89* (2006.01)
*G01S 7/52* (2006.01)

(52) U.S. Cl.
CPC ............ *A61B 8/445* (2013.01); *A61B 8/4488* (2013.01); *A61B 8/4494* (2013.01); *A61B 8/56* (2013.01); *G01S 7/52034* (2013.01); *G01S 15/8927* (2013.01); *G01S 15/8997* (2013.01)

(58) Field of Classification Search
USPC ......................................................... 367/11
See application file for complete search history.

(56) References Cited

U.S. PATENT DOCUMENTS

| | | |
|---|---|---|
| 6,547,730 B1 | 4/2003 | Lin et al. |
| 7,846,101 B2 | 12/2010 | Eberle et al. |
| 2003/0045794 A1 | 3/2003 | Bae |
| 2003/0149362 A1* | 8/2003 | Azuma .............. G01S 7/52047 600/437 |
| 2008/0114247 A1 | 5/2008 | Urbano et al. |
| 2009/0069692 A1 | 3/2009 | Cooley et al. |
| 2011/0077526 A1 | 3/2011 | Zwirn |
| 2012/0128223 A1 | 5/2012 | Rivaz et al. |

OTHER PUBLICATIONS

International Searching Authority/European Patent Office, "Communication—Supplementary European Search Report," for European Application No. 13831483.6, dated Aug. 25, 2016, 12 pages.

Karaman M. et al: "Synthetic aperture imaging for small scale systems", IEEE Transactions on Ultrasonics, Ferroelectronics and Frequency Control, IEEE, US, vol. 42, No. 3, May 1, 1995, pp. 429-442.

Chiao R. Y. et al: "Aperture formation on reduced-channel arrays using the transmit-receive apodization matrix", Ultrasonics Symposium, 1996. Proceedings., 1996 IEEE San Antonio, TX, USA Nov. 3-6, 1996, IEEE, New York, NY, USA, vol. 2, Nov. 3, 1996, pp. 1567-1571.

Iben Kraglund Holfort et al: "Adaptive receive and transmit apodization for synthetic aperture ultrasound imaging", Ultrasonics Symposium (IUS), 2009 IEEE International, IEEE, Piscataway, NJ, USA, Sep. 20, 2009, pp. 1-4.

\* cited by examiner

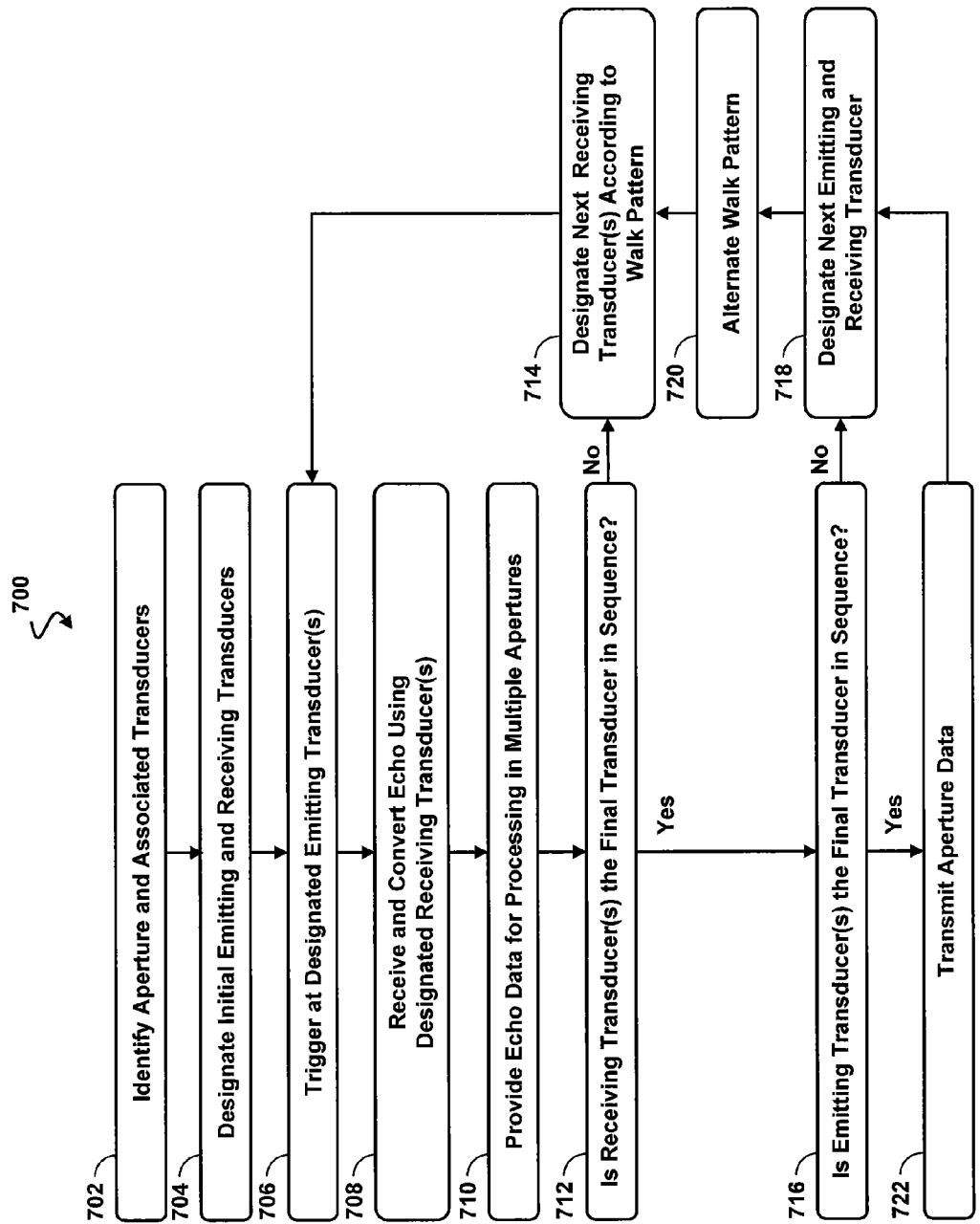

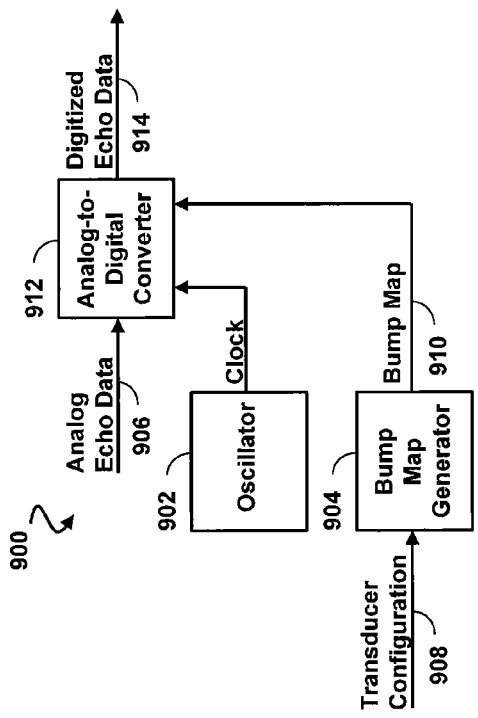
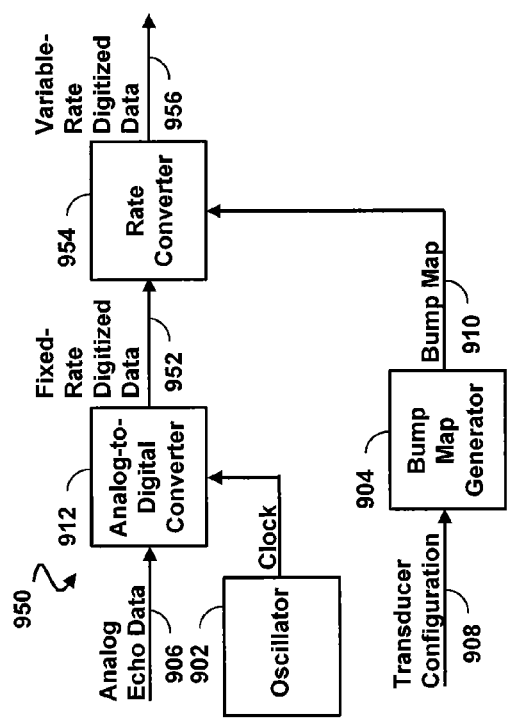
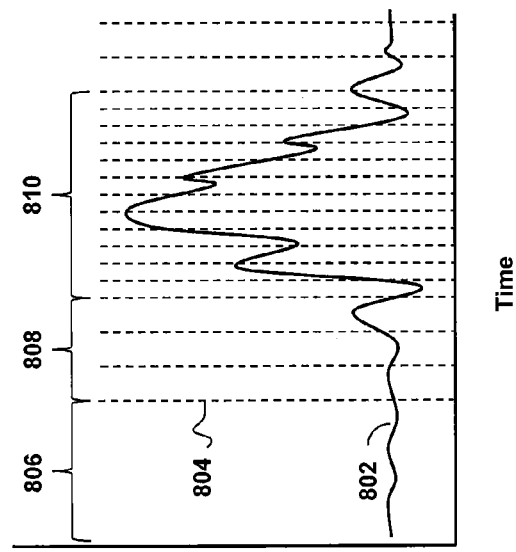

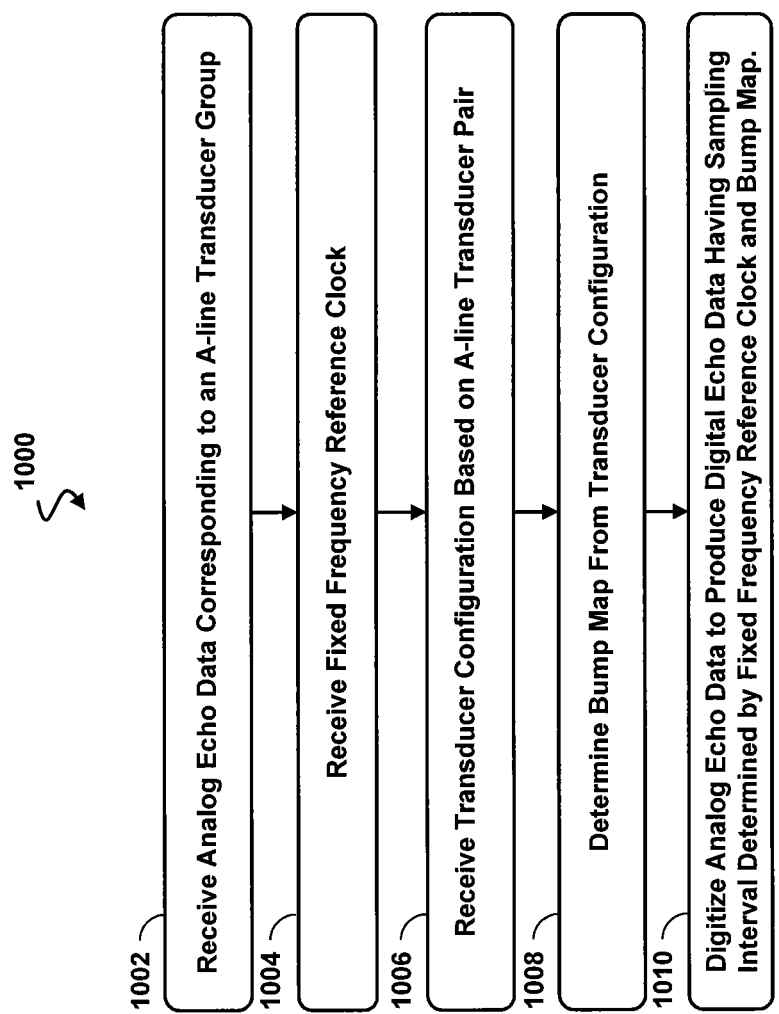

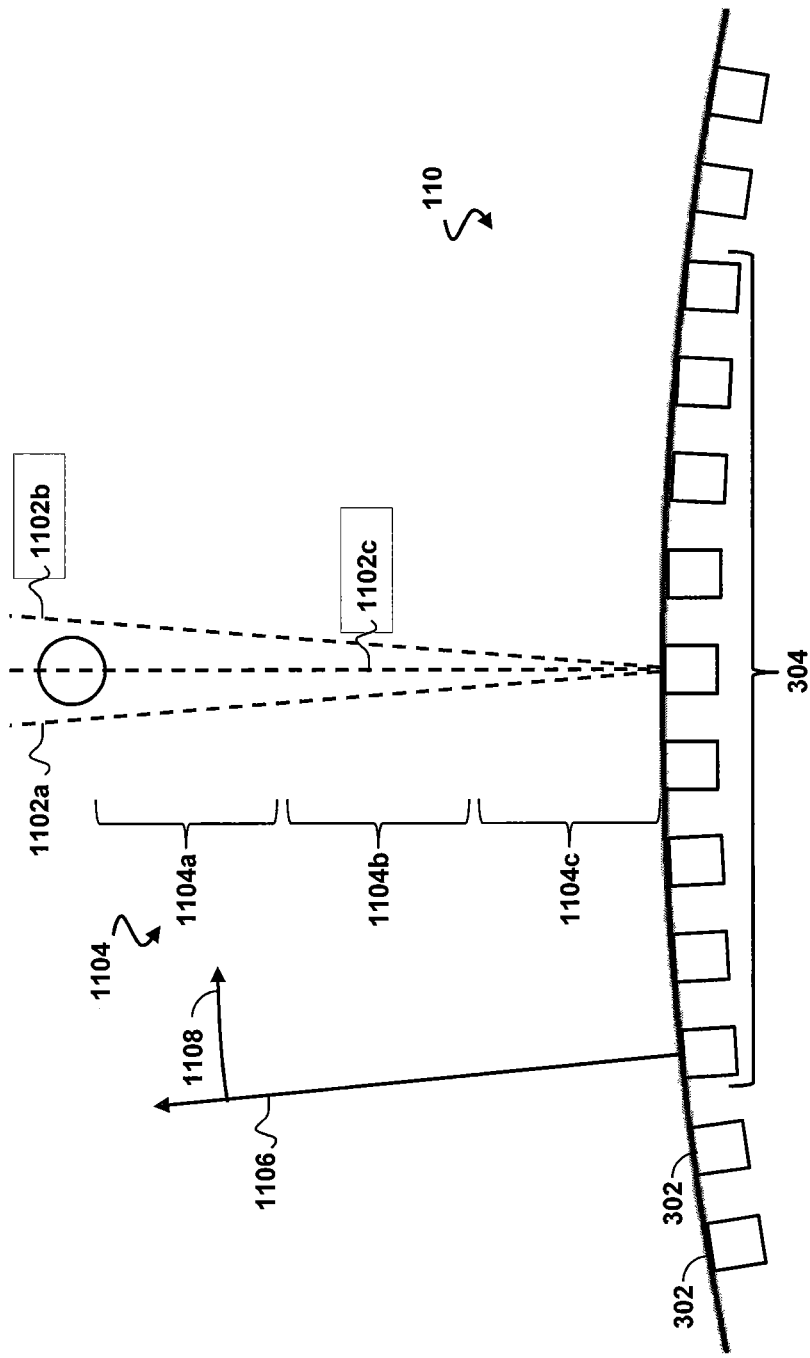

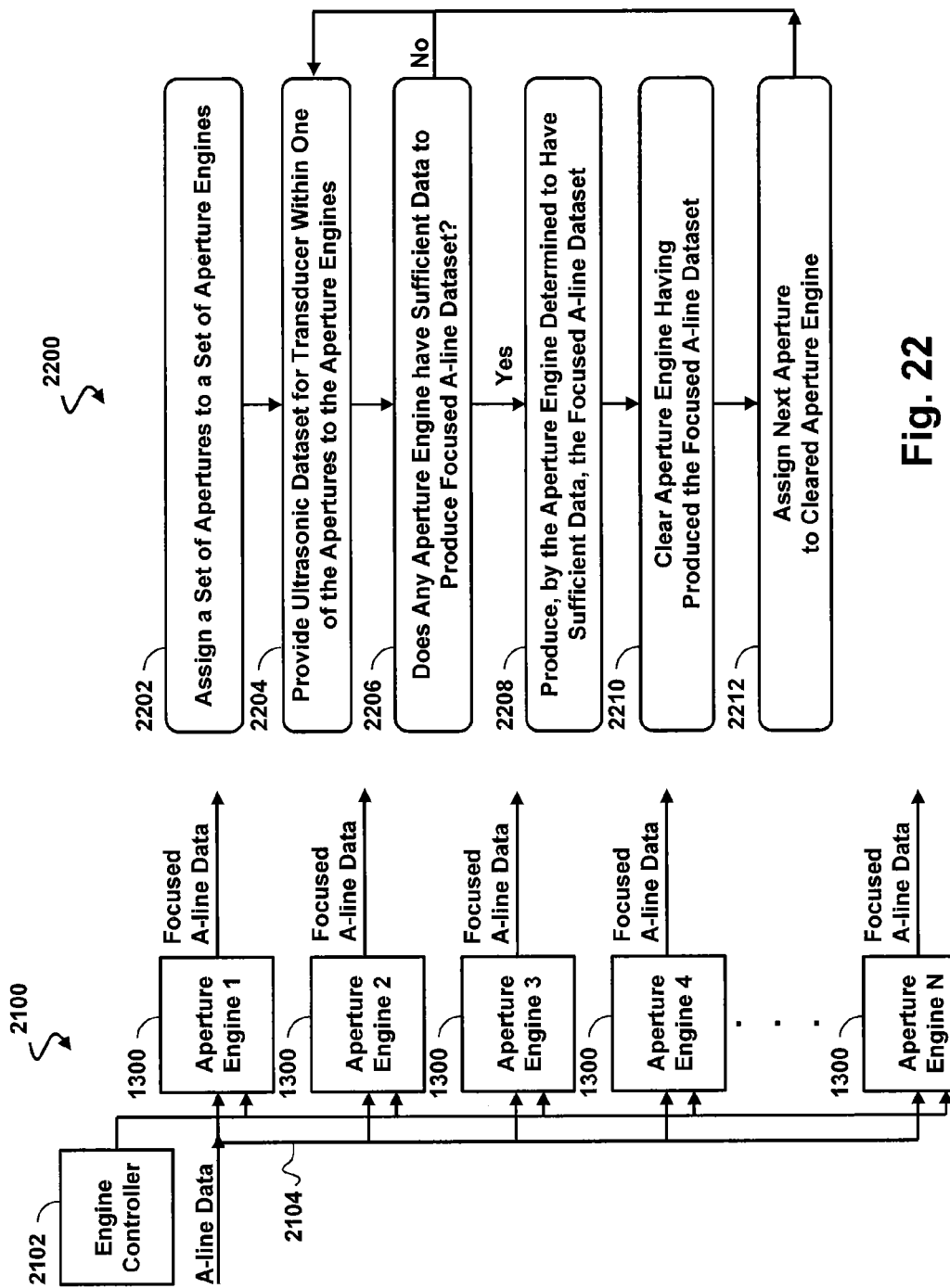

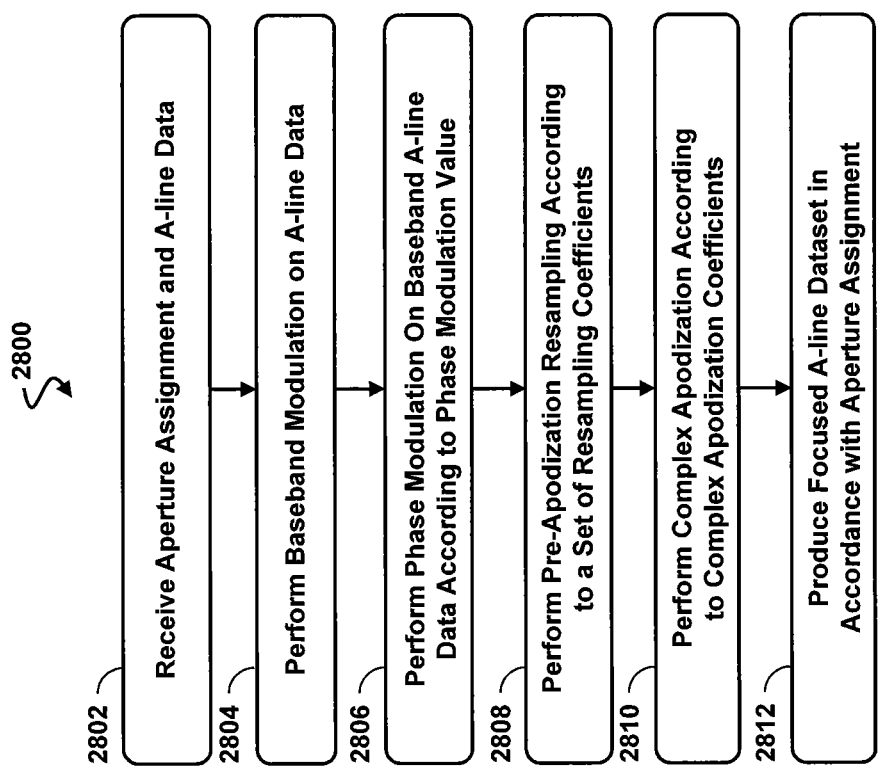

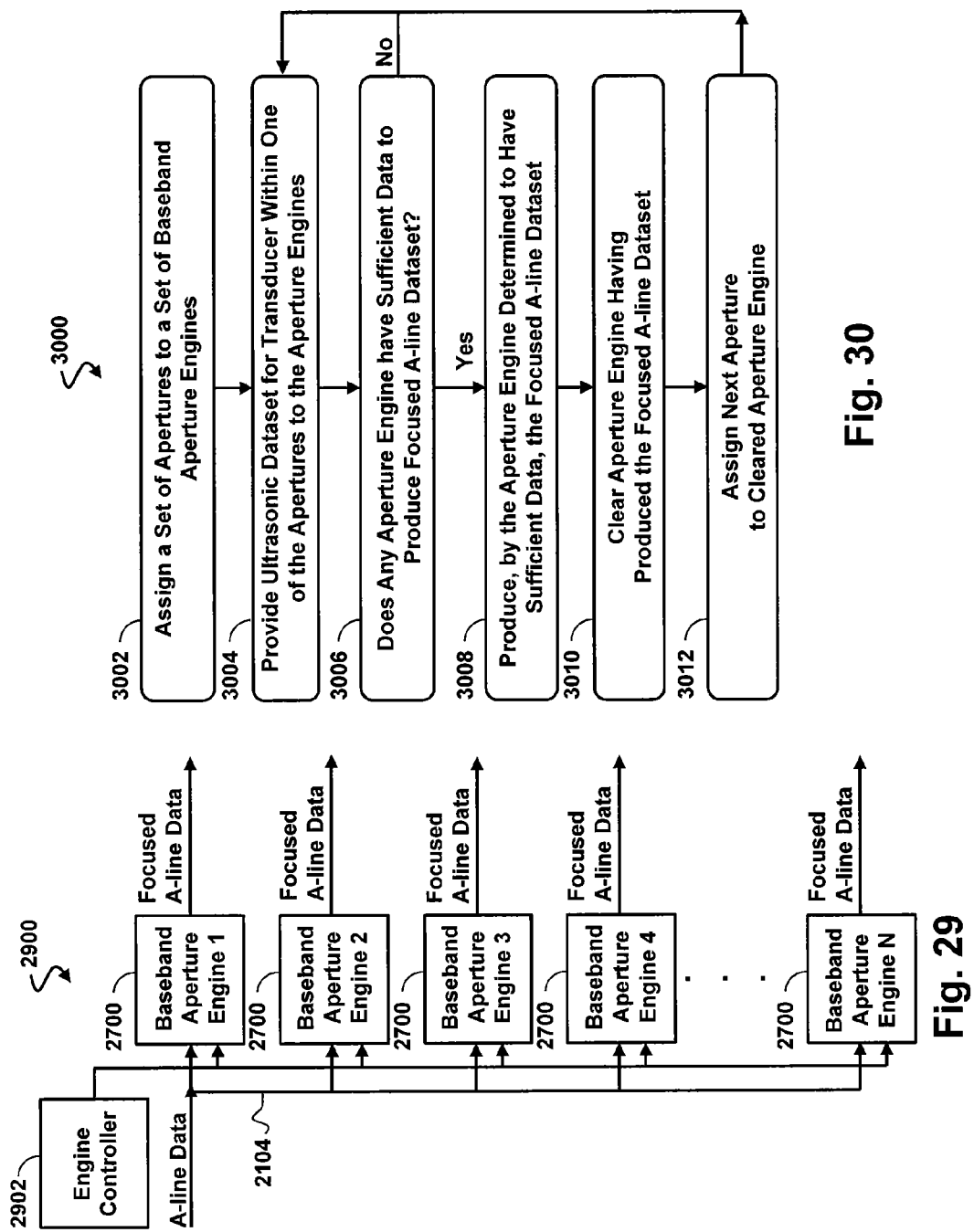

SYSTEM AND METHOD FOR FOCUSING ULTRASOUND IMAGE DATA

CROSS-REFERENCE TO RELATED APPLICATIONS

The present application is a continuation of U.S. patent application Ser. No. 13/974,757, filed Aug. 23, 2013, which claims priority to and the benefit of U.S. Provisional Patent Application No. 61/693,118, filed Aug. 24, 2012, each of which is hereby incorporated by reference in its entirety.

TECHNICAL FIELD

The present disclosure relates generally to intravascular ultrasound (IVUS) imaging and, in particular, to receiving and focusing ultrasound information to produce an image. In various embodiments, the focusing system receives information from an array of ultrasound transducers, such as piezoelectric micromachine ultrasound transducers (PMUTs), capacitive micromachined ultrasonic transducers (CMUTs), and piezoelectric zirconate transducers (PZTs). The focusing system processes the data to produce an ultrasound image. For example, some embodiments of the present disclosure provide an IVUS imaging system particularly suited to imaging a human blood vessel.

BACKGROUND

Intravascular ultrasound (IVUS) imaging is widely used in interventional cardiology as a diagnostic tool for assessing a diseased vessel, such as an artery, within the human body to determine the need for treatment, to guide the intervention, and/or to assess its effectiveness. An IVUS device including one or more ultrasound transducers is passed into the vessel and guided to the area to be imaged. The transducers emit ultrasonic energy in order to create an image of the vessel of interest. Ultrasonic waves are partially reflected by discontinuities arising from tissue structures (such as the various layers of the vessel wall), red blood cells, and other features of interest. Echoes from the reflected waves are received by the transducer and passed along to an IVUS imaging system. The imaging system processes the received ultrasound echoes to produce a cross-sectional image of the vessel where the device is placed.

There are two general types of IVUS devices in use today: rotational and solid-state (also known as synthetic aperture phased array). For a typical rotational IVUS device, a single ultrasound transducer element is located at the tip of a flexible driveshaft that spins inside a plastic sheath inserted into the vessel of interest. The transducer element is oriented such that the ultrasound beam propagates generally perpendicular to the axis of the device. The fluid-filled sheath protects the vessel tissue from the spinning transducer and driveshaft while permitting ultrasound signals to propagate from the transducer into the tissue and back. As the driveshaft rotates, the transducer is periodically excited with a high voltage pulse to emit a short burst of ultrasound. The same transducer then listens for the returning echoes reflected from various tissue structures. The IVUS imaging system assembles a two dimensional display of the vessel cross-section from a sequence of pulse/acquisition cycles occurring during a single revolution of the transducer.

In contrast, solid-state IVUS devices carry a transducer complex that includes an array of ultrasound transducers distributed around the circumference of the device connected to a set of transducer controllers. The transducer controllers select individual transducers for transmitting an ultrasound pulse and for receiving the echo signal. By stepping through a sequence of transmit-receive pairs, the solid-state IVUS system can synthesize the effect of a mechanically scanned transducer element but without moving parts. Since there is no rotating mechanical element, the transducer array can be placed in direct contact with the blood and vessel tissue with minimal risk of vessel trauma. Furthermore, because there is no rotating element, the interface is simplified. The solid-state scanner can be wired directly to the imaging system with a simple electrical cable and a standard detachable electrical connector.

Despite their wide acceptance, traditional solid-state IVUS imaging systems have been held back by the processing required to form a focused image from the received echoes. Processing and focusing the ultrasound data typically involves high-speed, high-performance computational cores connected to large memory banks. Such hardware is expensive to manufacture and has limited the quality of the image produced. Thus, while existing IVUS imaging systems have proven useful, there remains a need for improved resolution and performance, particularly when it can be delivered in a more economical system. Accordingly, the need exists for improvements to solid-state IVUS signal processing systems.

SUMMARY

Embodiments of the present disclosure provide a high-performance, high-efficiency temporal focusing engine, which may be used in applications such as a solid-state intravascular ultrasound imaging system.

In some embodiments, an ultrasound processing system is provided. The system includes first and second aperture engines; an A-line data interface providing at least a portion of A-line data to the first and second aperture engines; and an engine controller communicatively coupled to the first and second aperture engines. The engine controller provides at least first and second aperture assignments designating portions of the A-line data to the first and second aperture engines, respectively. The first and second aperture engines receive the first and second aperture assignments, respectively, receive the at least a portion of the A-line data, perform one or more focusing processes on the received A-line data, and produce focused data in accordance with the first and second aperture assignments, respectively. In one such embodiment, the engine controller further monitors to determine when one of the first and second aperture engines produces focused data, and provides a third aperture assignment to the one of the first and second aperture engines when it is determined that the one of the first and second aperture engines has produced focused data.

In some embodiments, a method of focusing ultrasound echo data is provided. The method comprises assigning a set of apertures to a set of aperture engines, providing an ultrasonic dataset for one or more transducer within the set of apertures to each of the aperture engines within the set of aperture engines, producing a focused A-line dataset when it is determined that a first aperture engine of the set of aperture engines has sufficient data to produce the focused A-line dataset, and thereafter assigning another aperture to the first aperture engine.

In some embodiments, a system for processing echo data is provided. The system comprises a means for performing focusing processes on an echo dataset; a means for unimpededly providing at least a portion of the echo dataset communicatively coupled to the means for performing focusing processes; and a means for performing a round-robin assignment of apertures by providing configuration information designating portions of the echo dataset to the means for performing focusing processes. The means for performing the round-robin assignment is communicatively coupled to the means for performing focusing processes.

In some embodiments, an ultrasound system is provided, the system comprising a set of first-level aperture engines; a set of second-level aperture engines communicatively coupled to one or more of the set of first-level aperture engines; an A-line data interface providing at least a portion of A-line data to each engine of the set of first-level aperture engines; and an engine controller communicatively coupled to each engine of the set of first-level aperture engines. The engine controller provides a sub-aperture assignment designating portions of the A-line data to each engine of the set of first-level aperture engines. The engines of the set of first-level aperture engines each: receive a provided sub-aperture assignment; receive the at least a portion of the A-line data; perform one or more first-level focusing process on the received A-line data; and produce partially-focused data in accordance with the provided sub-aperture assignment. The engines of the set of second-level aperture engines each: receive partially-focused data from the coupled engines of the set of first-level aperture engines, perform one or more second-level focusing processes on the received partially-focused data, and produce focused aperture data. In one such embodiment, the engine controller further monitors to determine when one engine of the set of first-level aperture engines produces partially focused data, and provides another sub-aperture assignment to the one engine of the set of first-level aperture engines when it is determined that the one engine has produced partially-focused data.

In some embodiments, a method of focusing ultrasound echo data is provided, the method comprising: assigning a set of sub-apertures to a set of first-level aperture engines; providing at least a portion of an ultrasonic dataset to each engine of the set of first-level aperture engines; producing a partially-focused A-line dataset when it is determined that a first first-level aperture engine of the set of first-level aperture engines has sufficient data to produce the partially-focused A-line dataset; thereafter assigning another sub-aperture to the first first-level aperture engine; receiving the partially-focused A-line dataset at a first second-level aperture engine of the set of second-level aperture engines; and producing a focused A-line dataset when it is determined that the first second-level aperture engine has sufficient data to produce the focused A-line dataset.

In some embodiments, a system is provided comprising: a bump map generator receiving a transducer configuration specifying a emitter/receiver transducer pair and producing a bump map based on the transducer configuration; a clock signal generator producing a fixed-frequency clock having a clock frequency; and an analog-to-digital converter that performs: receiving analog data corresponding to the emitter/receiver transducer pair; and producing digital data based on the analog data having a sample rate determined by the fixed-frequency clock and the bump map.

In some embodiments, a method is provided comprising: receiving analog echo data corresponding to an emitter/receiver transducer pair; receiving a fixed-frequency reference clock having a clock frequency; receiving a transducer configuration based on the emitter/receiver transducer pair; determining a bump map from the transducer configuration; and digitizing the analog echo data to produce digital echo data. The digital echo data has a sampling interval determined by the fixed-frequency reference clock and the bump map.

In some embodiments, an ultrasound processing system is provided. The system comprises a digital data interface receiving digital ultrasound echo data; and a frequency converter communicatively coupled to the digital data interface. The frequency converter receives the digital ultrasound echo data and a measure of resolution for a display image and resamples the digital ultrasound echo data to produce resampled digital ultrasound echo data having a sampling interval based on the measure of resolution.

In some embodiments, a method is provided comprising: receiving digital ultrasound echo data; receiving a measure of resolution for a display image; and resampling the digital ultrasound echo data based on the measure of resolution.

In some embodiments, a system for resampling ultrasound data is provided. The system comprises a signal interface receiving an ultrasound data stream; a coefficient interface receiving a set of weighting coefficients; and a weighted interpolation network communicatively coupled to the signal interface and the coefficient interface. The weighted interpolation network includes a plurality of delay devices delaying the ultrasound data stream, wherein the delaying produces a plurality of delayed ultrasound data streams; a plurality of weighting units applying the set of weighting coefficients to the plurality of delayed ultrasound data streams, wherein the applying produces a plurality of weighted ultrasound data streams; and a summing unit adding the plurality of weighted ultrasound data streams to produce a resampled ultrasound data stream.

In some embodiments, a method of processing ultrasound data is provided. The method comprises: receiving digital ultrasound data; delaying the digital ultrasound data by a first delay amount to produce first delayed digital ultrasound data; applying a first weighting to the first delayed digital ultrasound data to produce first weighted ultrasound data; delaying the digital ultrasound data by a second delay amount to produce second delayed digital ultrasound data; applying a second weighting to the second delayed digital ultrasound data to produce second weighted ultrasound data; and adding the first and second weighted ultrasound data to produce resampled digital ultrasound data.

In some embodiments, an ultrasound processing system is provided. The system comprises: first and second baseband aperture engines; an A-line data interface providing at least a portion of A-line data to the first and second aperture engines; and an engine controller communicatively coupled to the first and second aperture engines. The engine controller provides first and second aperture assignments designating portions of the A-line data to the first and second aperture engines, respectively. The first and second baseband aperture engines receive the first and second aperture assignments, respectively; receive the at least a portion of the A-line data, perform one or more baseband focusing processes on the received A-line data; and produce focused data in accordance with the first and second aperture assignments, respectively. In one such embodiment, the engine controller further monitors to determine when one of the first and second baseband aperture engines produces focused data, and provides a third aperture assignment to the one of the first and second baseband aperture engines when it is determined that the one of the first and second baseband aperture engines has produced focused data.

In some embodiments, a method of focusing ultrasound echo data is provided. The method comprises: assigning a set of apertures to a set of baseband aperture engines;

providing an ultrasonic dataset for one or more transducer within the set of apertures to each of the baseband aperture engines within the set of baseband aperture engines; producing a focused A-line dataset when it is determined that a first engine of the set of baseband aperture engines has sufficient data to produce the focused A-line dataset; and thereafter assigning another aperture to the first engine.

Some embodiments of the present disclosure incorporate a parallel arrangement of aperture engines performing focusing calculations according to round-robin aperture assignments in order to achieve high resource utilization and optimal throughput. The parallel arrangement of focusing engines takes advantage of the highly parallel nature of focusing processes. In some embodiments, the aperture engines selectively obtain echo data from a common bus based on the aperture assignment, which avoids the need for data steering circuitry. The simplified data bus allows for more implementation options. For example, in some embodiments, each aperture engine is implemented on a separate low-cost device such as an ASIC, FPGA, DSP, microcontroller, or CPU, whereas, in some embodiments, multiple aperture engines are implemented on a single device, such as an ASIC, FPGA, DSP, microcontroller, or CPU.

Further embodiments utilize a hierarchical arrangement of parallel aperture engines to divide focusing computations. This configuration allows further flexibility in implementation. For example, in some embodiments, lower level focusing is performed near to the transducers, such as in the transducer complex or on the wire. Digitization of echo data close to the transducers may reduce line loss and transmission noise, and such embodiments may also simplify the interface between the IVUS device and the remainder of the IVUS system. In some embodiments, lower-level engines are part of a sterile package and operate within a sterile field, while upper level engines are located outside the sterile field, such as in an adjacent observation area. The simplified interface of a hierarchical arrangement reduces the number of wires that cross the sterile boundary. In embodiments utilizing a wireless interface, potential avenues for contamination are further reduced.

Various embodiments utilize intelligent resampling to reduce the dataset required to represent digitized echo data. In some embodiments, this reduces data handling thereby allowing reductions in bus width, bus speed, bus buffering, and/or data storage. In some embodiments, reduced data size allows reduction in processing resources allocated to focusing tasks such as time-of-flight adjustment, apodization, and summation. In turn, this may deliver smaller, more economical, and more energy-efficient implementations.

Some embodiments of the present disclosure reduce the size of the echo dataset without adversely affecting the quality of the focused echo data by utilizing variable-rate digitization of analog echo data. In some embodiments, variable-rate digitization is performed utilizing fixed-rate components through the use of a bump map. This implementation may convey additional advantages as fixed-rate components may draw less power, may avoid complex control circuitry, and may exhibit improved durability and longevity when compared to variable-rate equivalents.

Some embodiments of the present disclosure reduce the size of the echo dataset by accounting for the resolution of the final image. The final image is composed of pixels, which are regions of uniform color and intensity. Accordingly, in some embodiments, data beyond an amount needed to determine a pixel can be discarded without affecting the final image. This can result in improved efficiency, reduced system size, and reduced cost. In an embodiment, per-pixel resampling allows a mid-range imaging system to produce a high-resolution image such one configured for a high-definition display.

Some embodiments of the present disclosure manage the size of the echo dataset by performing an interpolated phase shift as an alternative to upsampling. The interpolated phase shift provides increased data granularity without the higher data rate associated with upsampling. In some embodiments, this retains the benefits of the lower bit-rates including lower clock frequencies, reduced data steering, decreased circuit complexity, and reduced memory requirements. As another advantage, certain focusing steps may benefit from increased data granularity while others may benefit from lower bit rates. Instead of resampling prior to each focusing step, in some embodiments, the interpolated phase shift replaces an upsampling process followed by a downsampling process.

Further embodiments extend the round-robin architecture and scheduling to baseband focusing of echo data. Because baseband representations of echo data have lower characteristic frequencies, digital sampling rates can be reduced. The reduced sampling rate may accordingly reduce bus speed, data storage requirements, clock frequency, power consumption, and/or processing hardware required for other focusing steps.

Additional aspects, features, and advantages of the present disclosure will become apparent from the following detailed description.

BRIEF DESCRIPTION OF THE DRAWINGS

Illustrative embodiments of the present disclosure will be described with reference to the accompanying drawings, of which:

FIG. 7 is a flow diagram of a method of collecting ultrasound data for multiple apertures concurrently according to aspects of the present disclosure.

FIG. 8 is a plot of received transducer echo data over time according to aspects of the present disclosure.

FIGS. 9a and 9b are schematic diagrams of variable-clock-rate digitizers according to aspects of the present disclosure.

FIG. 10 is a flow diagram of a method of generating variable-rate digitized ultrasound data according to aspects of the present disclosure.

FIG. 11 is a cross-sectional view of a focused aperture of a transducer complex according to aspects of the present disclosure.

FIG. 21 is a schematic of a focusing system according to aspects of the present disclosure.

FIG. 22 is a flow diagram of a method for focusing multiple apertures according to aspects of the present disclosure.

FIG. 28 is a flow diagram of a method of baseband aperture focusing according to aspects of the present disclosure.

FIG. 29 is a schematic of a baseband focusing system according to aspects of the present disclosure.

FIG. 30 is a flow diagram of a method for focusing multiple apertures according to aspects of the present disclosure.

DETAILED DESCRIPTION

Figure 1:
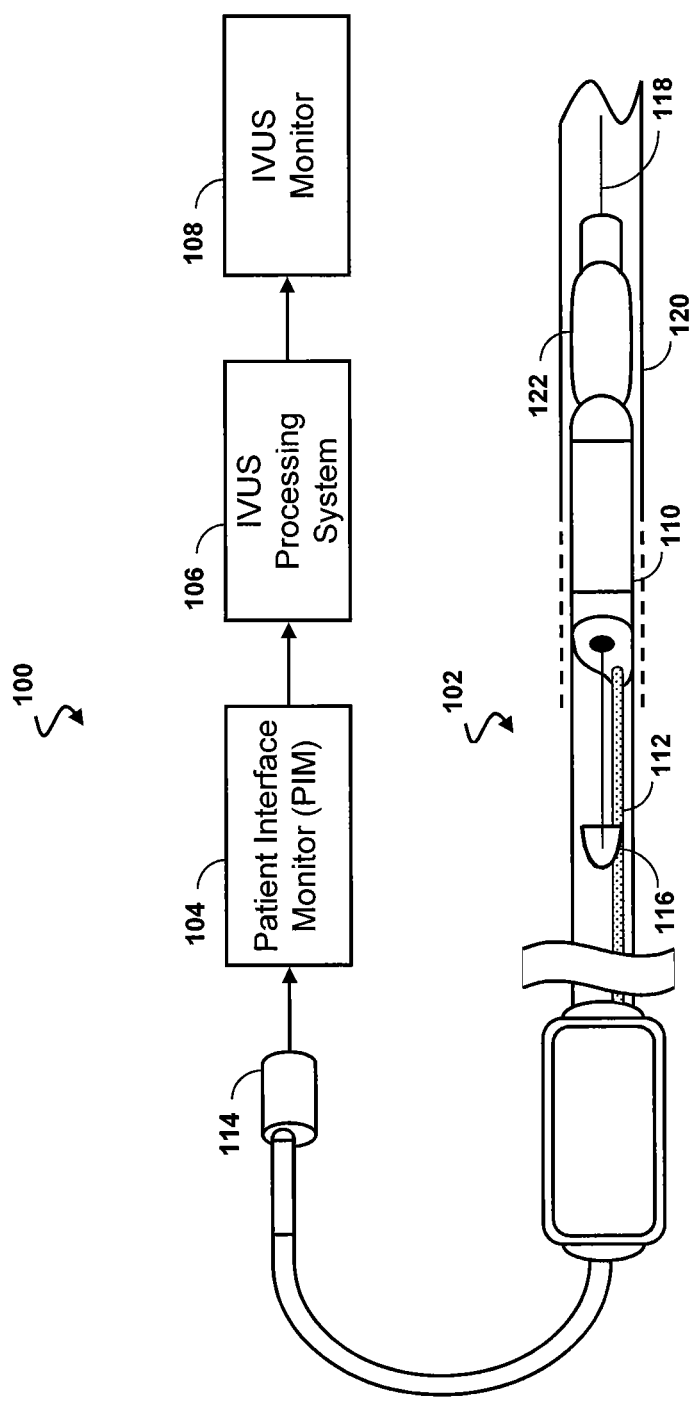
FIG. 1 is a diagrammatic schematic view of an imaging system according to aspects of the present disclosure.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. For example, while the focusing system is described in terms of cardiovascular imaging, it is understood that it is not intended to be limited to this application. The system is equally well suited to any application requiring imaging within a confined cavity. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

FIG. 1 is a diagrammatic schematic view of an intravascular ultrasound (IVUS) imaging system 100 according to aspects of the present disclosure. In some embodiments of the present disclosure, the IVUS imaging system 100 is a piezoelectric micromachine ultrasound transducer (PMUT) solid-state IVUS imaging system. In some embodiments, the IVUS imaging system 100 is a CMUT or PZT solid-state IVUS imaging system. The IVUS imaging system 100 may include an IVUS device 102 such as a catheter, guide wire, or guide catheter, a patient interface module (PIM) 104, an IVUS processing system or console 106, and/or a monitor 108.

At a high level, the IVUS device 102 emits ultrasonic energy from a transducer complex 110 near the tip of the device. The ultrasonic energy is reflected by structures within the environment surrounding the transducer complex 110. The transducer complex 110 also receives and measures the reflected waves.

The PIM 104 facilitates communication of signals between the IVUS console 106 and the IVUS device 102 to control the operation of the transducer complex 110. This includes transferring echo data detected by the transducer complex 110 to the IVUS console 106. In that regard, the PIM 104 forwards the echo data received and, in some embodiments, performs preliminary processing of the echo data prior to transmitting the data to the console 106. In examples of such embodiments, the PIM 104 performs amplification, filtering, and/or aggregating of the data. In an embodiment, the PIM 104 also supplies high- and low-voltage DC power to support operation of the device 102 including circuitry within the transducer complex 110.

The IVUS console 106 receives the echo data from the transducer complex 110 by way of the PIM 104 and processes the data to create an image of the environment surrounding the transducer complex 110. The console 106 may also display the image on the monitor 108.

In some embodiments, the IVUS device includes some features similar to traditional solid-state IVUS catheters, such as the EagleEye® catheter available from Volcano Corporation and those disclosed in U.S. Pat. No. 7,846,101 hereby incorporated by reference in its entirety. For example, the IVUS device 102 includes the transducer complex 110 at a distal end of the device 102 and a transmission line bundle 112 extending along the longitudinal body of the device 102. The transmission line bundle 112 terminates in a PIM coupler 114 at a proximal end of the device 102. The PIM coupler 114 electrically couples the transmission line bundle 112 to the PIM 104 and physically couples the IVUS device 102 to the PIM 104. In an embodiment, the IVUS device 102 further includes a guide wire exit port 116. Accordingly, in some instances the IVUS device is a rapid-exchange catheter. The guide wire exit port 116 allows a guide wire 118 to be inserted towards the distal end in order to direct the device 102 through a vessel 120. Vessel 120 represents fluid filled or surrounded structures, both natural and man-made, within a living body that may be imaged and can include for example, but without limitation, structures such as: organs including the liver, heart, kidneys, gall bladder, pancreas, lungs; ducts; intestines; nervous system structures including the brain, dural sac, spinal cord and peripheral nerves; the urinary tract; as well as valves within the blood or other systems of the body. In addition to imaging natural structures, the images may also include imaging man-made structures such as, but without limitation, heart valves, stents, shunts, filters and other devices positioned within the body, for example, a guide wire or guide catheter. In an embodiment, the IVUS device 102 also includes an inflatable balloon portion 122 near the distal tip. The balloon portion 122 is open to a duct that travels along the length of the IVUS device and ends in an inflation port (not shown). The balloon 122 may be selectively inflated and deflated via the inflation port.

The IVUS processing system 106 is designed to operate in conjunction with the IVUS device 102 to produce high-resolution images from within narrow passageways. To advance the performance of IVUS imaging devices compared to the current state of the art, embodiments of the present disclosure incorporate advanced transducer technologies, such as PMUT, that offer wide bandwidth (>100%) and a spherically-focused aperture. The broad bandwidth is important for producing a short ultrasound pulse to achieve optimum resolution in the radial direction, and the spherically focused aperture provides optimum resolution in the lateral and elevation dimensions. The improved resolution provided by PMUT and other advanced ultrasound transducer technologies facilitates better diagnostic accuracy, enhances the ability to discern different tissue types, and enhances the ability to accurately ascertain the borders of the vessel lumen. Embodiments of the present disclosure also provide an improved focusing engine within the IVUS processing system 106, which improves focusing resolution, reduces noise and artifacts, and delivers increased resolution and frame rate while utilizing more efficient and more economical components.

Figure 2:
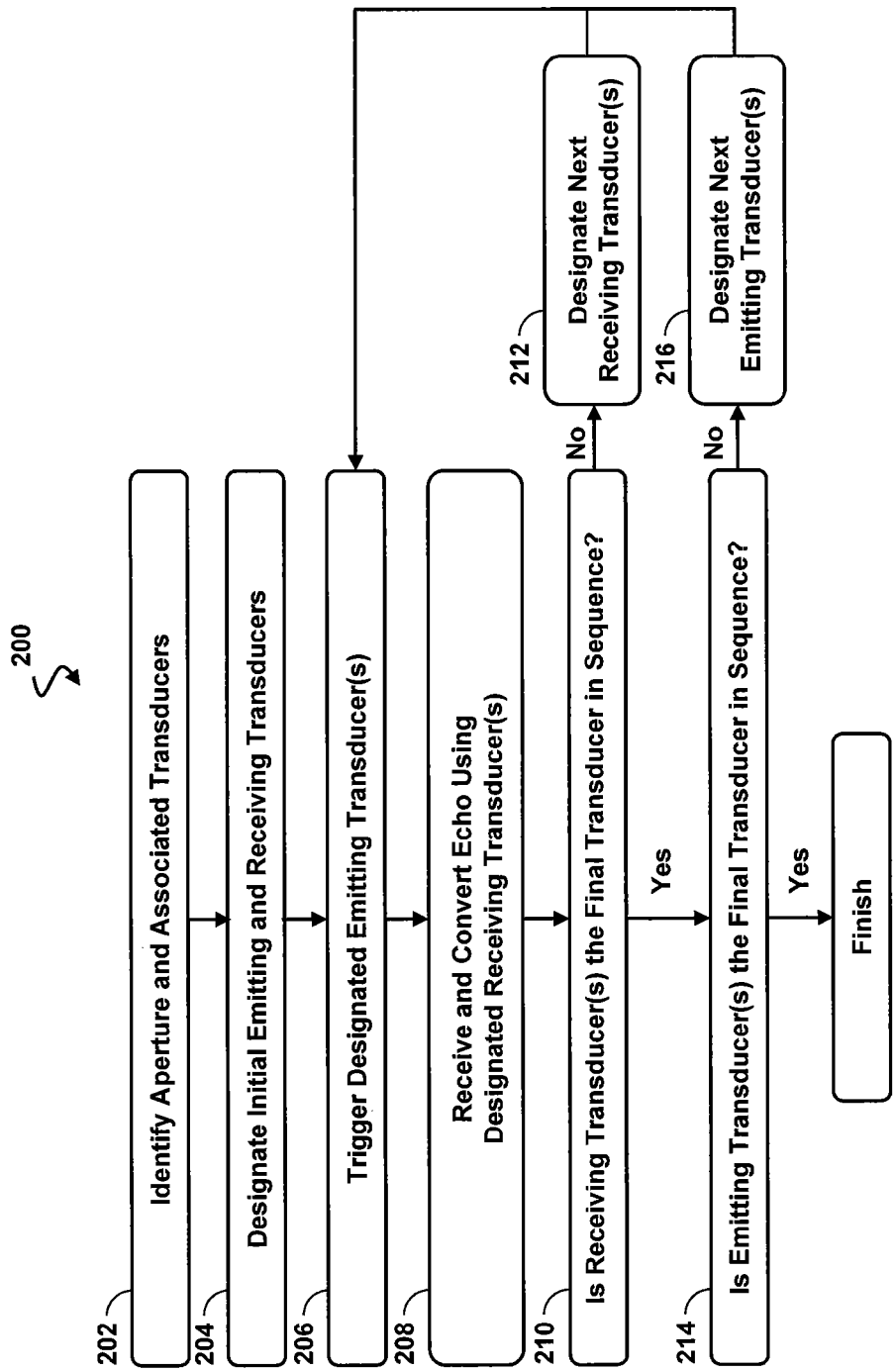
FIG. 2 is a flow diagram of a method of generating ultrasound data according to aspects of the present disclosure.
Figure 3:
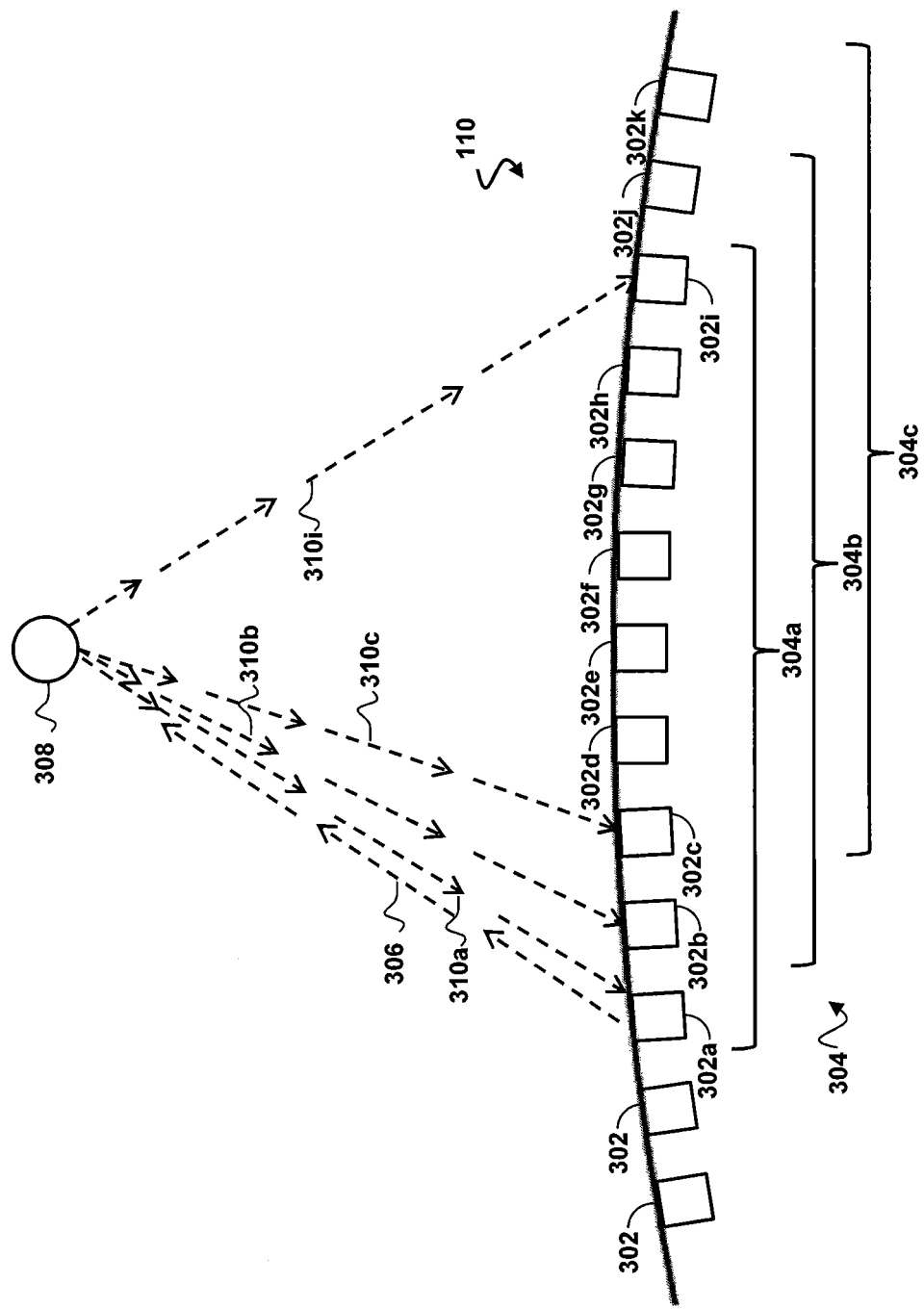
FIG. 3 is a radial cross-sectional view of a portion of a transducer complex according to aspects of the present disclosure.
Figure 4:
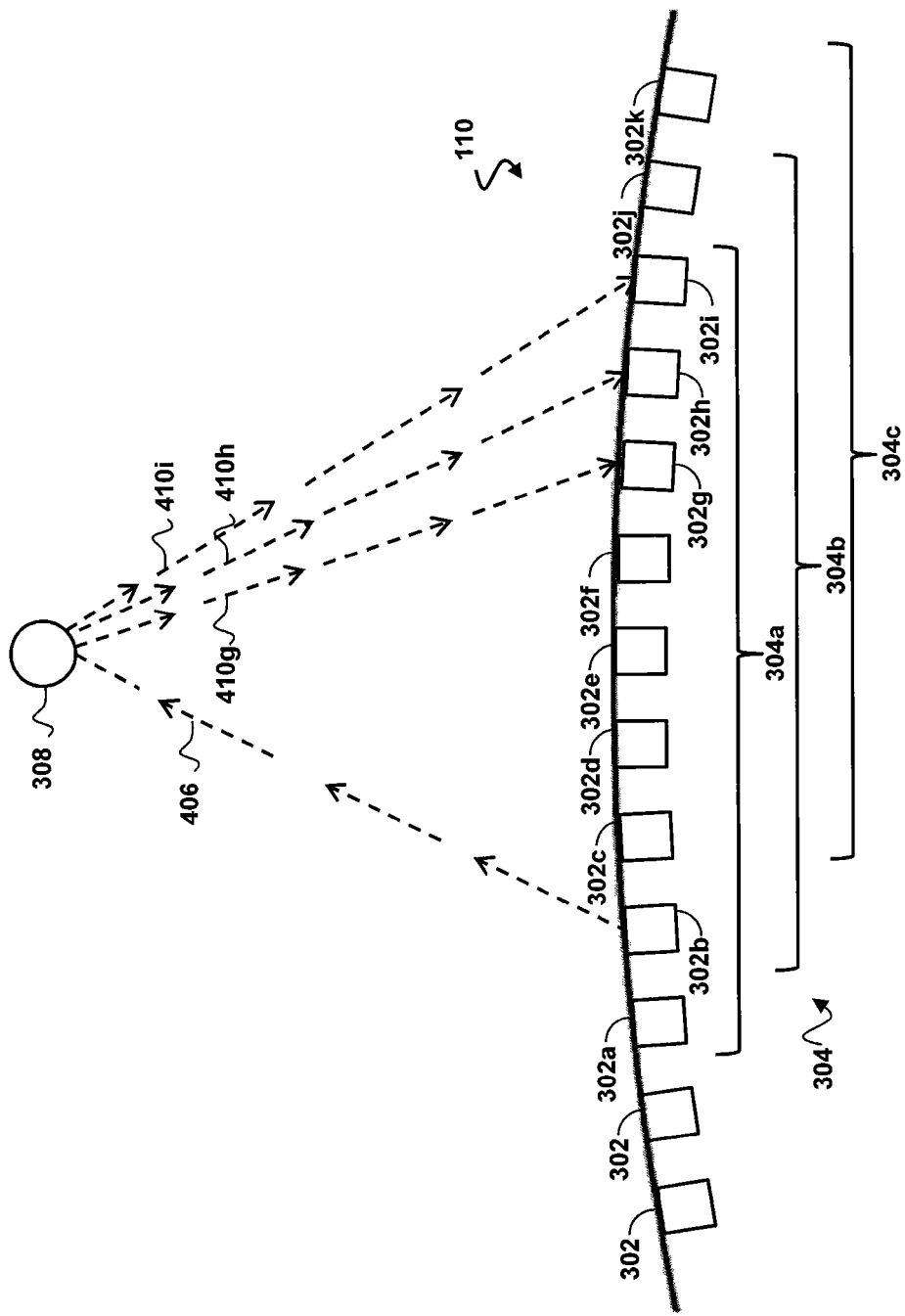
FIG. 4 is a radial cross-sectional view of a portion of a transducer complex according to aspects of the present disclosure.

A method of collecting ultrasound data is described with reference to FIGS. 2, 3, and 4. FIG. 2 is a flow diagram of a method 200 of generating ultrasound data according to aspects of the present disclosure. It is understood that additional steps can be provided before, during, and after the steps of method 200, and some of the steps described can be replaced or eliminated for other embodiments of the method. FIGS. 3 and 4 are radial cross-sectional views of a portion of a transducer complex 110 according to aspects of the present disclosure.

The transducer complex 110 houses an array of transducers 302, thirteen of which are illustrated in FIG. 3. The transducers 302 are grouped into apertures 304, including apertures 304a, 304b, and 304c. In some embodiments, each transducer 302 may be part of one or more apertures 304. For example, transducer 302c is included in apertures 304a, 304b, and 304c. By way of non-limiting example, in the illustrated embodiment, each aperture 304 contains nine transducers 302. Other aperture widths are contemplated. For example, further embodiments have apertures 304 containing 8, 10, 12, 14, 16, or 32 transducers 302. In an embodiment, an aperture 304 contains 128 transducers 302.

Referring to block 202 and FIG. 3, the aperture 304 and the associated transducers 302 within the aperture are identified. This may include determining which particular transducer is located at each end of the aperture. Referring to FIG. 3, for exemplary aperture 304a, transducer 302a is at a first end, and transducer 302i is located at a second end. In block 204, initial emitting and receiving transducers are designated. Groupings of emitting and receiving transducers are referred to as A-lines. Within an A-line, more than one emitting transducer and more than one receiving transducer may be configured to act together. Furthermore, in some embodiments, a transducer may be designated as both an emitting and a receiving transducer. Accordingly, in an exemplary firing, transducer 302a is both the initial emitting transducer and the initial receiving transducer.

In block 206, the designated emitting transducer (in the current example, transducer 302a) or transducers are triggered to emit ultrasonic energy. A portion of the ultrasonic energy (e.g., the portion directed along the line indicated by arrows 306) is reflected by a target structure 308 located in the environment surrounding the transducer complex 110. In block 208, the designated receiving transducer (in the current example, transducer 302a) or transducers receive the reflected ultrasonic echo (indicated by arrows 310a). For the purposes of this disclosure, the act of receiving by a transducer may include experiencing an energy impulse such as an ultrasonic echo, converting the received impulse into a signal such as an electric potential, transmitting the converted signal, measuring the converted signal, and/or other suitable receiving steps. In some embodiments, a plurality of emitting transmitters is fired as a group. Firing transducers as a group may create a stronger ultrasonic transmission. Particularly in, but not limited to, embodiments using relatively small emitting transducers and/or embodiments imaging relatively long distances, a stronger emission improves the signal-to-noise ratio. Similarly, in some embodiments, a plurality of receiving transducers is set to receive as a group. The group of transducers may produce a stronger electrical potential with a better imaging characteristics than individual transducers acting alone.

In the illustrated embodiment, a sequence of firings are produced for each emitting transducer using a series of receiving transducers. The receiving transducers are stepped through according to a walk pattern. An exemplary walk pattern, which may be designated a forward walk, advances transducers in an arbitrary first direction (e.g., from transducer 302a to 302b to 302c). A backward walk advances transducers in a direction opposite the first direction (e.g., from transducer 302c to 302b to 302a). Other walk patterns utilize more than one direction, skip transducers, repeat transducers, group transducers and/or operate according to any other suitable pattern. When the receive cycle is complete, the next emitting transducer is selected.

Accordingly, in block 210, it is determined whether the current receiving transducer or transducers are the final transducer in the walk pattern. In some exemplary pattern, the final transducer in the pattern is the transducer at an end of the aperture (e.g., transducer 302a and/or transducer 302i for aperture 304a). In some exemplary patterns, the final receiving transducer is the emitting transducer. If the receiving transducer is not the final transducer in the pattern, in block 212, the next receiving transducer or transducers are designated according to the walk pattern. In the embodiment depicted in FIG. 3, according to a forward walk pattern, transducer 302b is designated as the next receiving transducer.

From block 212, the transmit and receive sequence of blocks 206 and 208 is repeated using the newly designated transmitter and receiver pair. In the illustrated embodiment of FIG. 3, an emission from transducer 302a (indicated by arrows 306) is reflected by the target structure 308. The reflection is received and converted by transducer 302b (indicated by arrows 310b). In the next iteration, emissions from transducer 302a are received by transducer 302c (indicated by arrows 310c). This proceeds until the forward walk pattern reaches transducer 302i (indicated by arrows 310i), which is the final receiving transducer in the aperture 304a. This completes the receive cycle for emitting transducer 302a.

Upon completion of the receive cycle, the method proceeds from block 210 to block 214 where it is determined whether the emitting transducer or transducers are the final emitting transducer according to an emitter walk pattern. In some embodiments, the final emitting transducer in the pattern is the transducer at an end of the aperture. If the emitting transducer is not the final transducer, in block 216, the next emitting transducer is designated. In some embodiments, this includes modifying an aspect of the receiver walk pattern as well. The walk pattern of the receiving transducers may be switched, for example, by switching from a forward walk pattern to a backward walk pattern. A new receiving transducer may also be designated. For example, the receiving transducer may be changed from transducer 302i to 302a when the emitting transducer changes. Other embodiments incorporate further modifications to the receive sequence.

Referring now to FIG. 4, in the illustrated embodiment, transducer 302b is designated the next emitting transducer, and the receiver walk pattern is switched to a backward walk pattern. In this embodiment, the designated receiving transducer, 302i, remains unchanged. In block 206, emitting transducer 302b creates an ultrasound emission (indicated by arrows 406), which is reflected by the target structure 308 and received by transducer 302i (indicated by arrows 410i). Because of the backward walk pattern, in the next iteration, the emissions from transducer 302b are received by transducer 302h (indicated by arrows 410h) and subsequently transducer 302g (indicated by arrows 410g). The method continues until final emitting transducer has completed a receive cycle, and, in some embodiments, the A-line combinations of emitting transducers and receiving transducers within the aperture are exhausted.

It is understood that disclosing the method 200 in terms of stepping through receiving transducer for a designated emitting transducer is purely arbitrary. In some embodiments, a receiving transducer is designated and the method 200 proceeds through a sequence of emitting transducers before designating a new receiving transducer. Furthermore, the emitter and receiver walk patterns disclosed with reference to FIGS. 3-4 are examples selected for clarity of illustration. Other walk patterns are contemplated and provided for.

As can be seen, for each of the exemplary nine-transducer apertures 304, 81 transducer combinations (or A-lines) exist. In some embodiments, the number of A-line firings is reduced by assuming that A-line data exhibits a reciprocal nature. In other words, a signal emitted by transducer 302a and received by transducer 302i may be a suitable substitute for a signal emitted by transducer 302i and received by transducer 302a. Thus, in some embodiments, only one A-line for each reciprocal A-line pair is generated.

Figure 5:
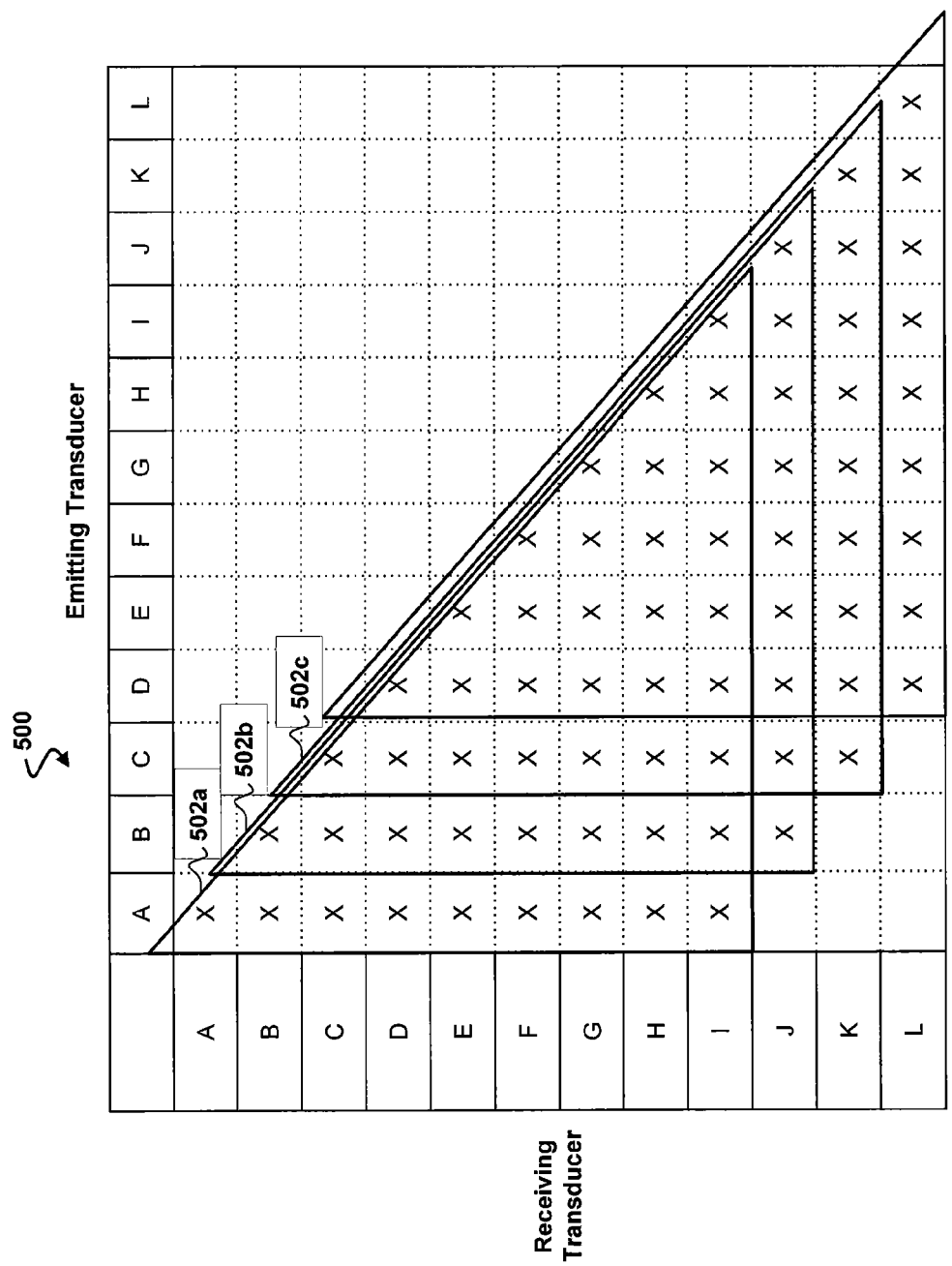
FIG. 5 is an aperture diagram of a transducer complex according to aspects of the present disclosure.

FIG. 5 is an aperture diagram 500 of a transducer complex 110 according to aspects of the present disclosure. FIG. 5 illustrates the relationship between transducer pairs (A-lines) and the associated apertures and the relationship between adjacent apertures. As can be seen, the aperture diagram 500 of FIG. 5 leverages the reciprocal nature of the data to reduce the number of A-line firings. In the illustrated embodiment, for an aperture having N transducers and an initial transducer index of i, signals generated by transducer $T_i$ are received by each transducer between $T_i$ and $T_{i+N-1}$ inclusive. Signals generated by a subsequent transducer $T_{i+1}$ are received by each transducer between $T_{i+1}$ and $T_{i+N-1}$ inclusive, but not necessarily by $T_i$ because suitable substitute data from $T_i$ to $T_{i+1}$ exists. Accordingly, the signal generated by $T_{i+N-1}$ is received by $T_{i+N-1}$, but not necessarily at the other transducers. Put in the context of FIG. 5, a first exemplary nine-transducer aperture includes transducers $T_A$ through $T_I$ and is represented by triangle 502a. Signals generated by transducer $T_A$ are received by transducers $T_A$ through $T_I$. Signals generated by transducer $T_B$ are received by transducers $T_B$ through $T_I$, and so on. As can be seen, the firing pattern incorporates only 45 firings instead of 81. This can measurably reduce the time required to obtain an aperture dataset.

Figure 6:
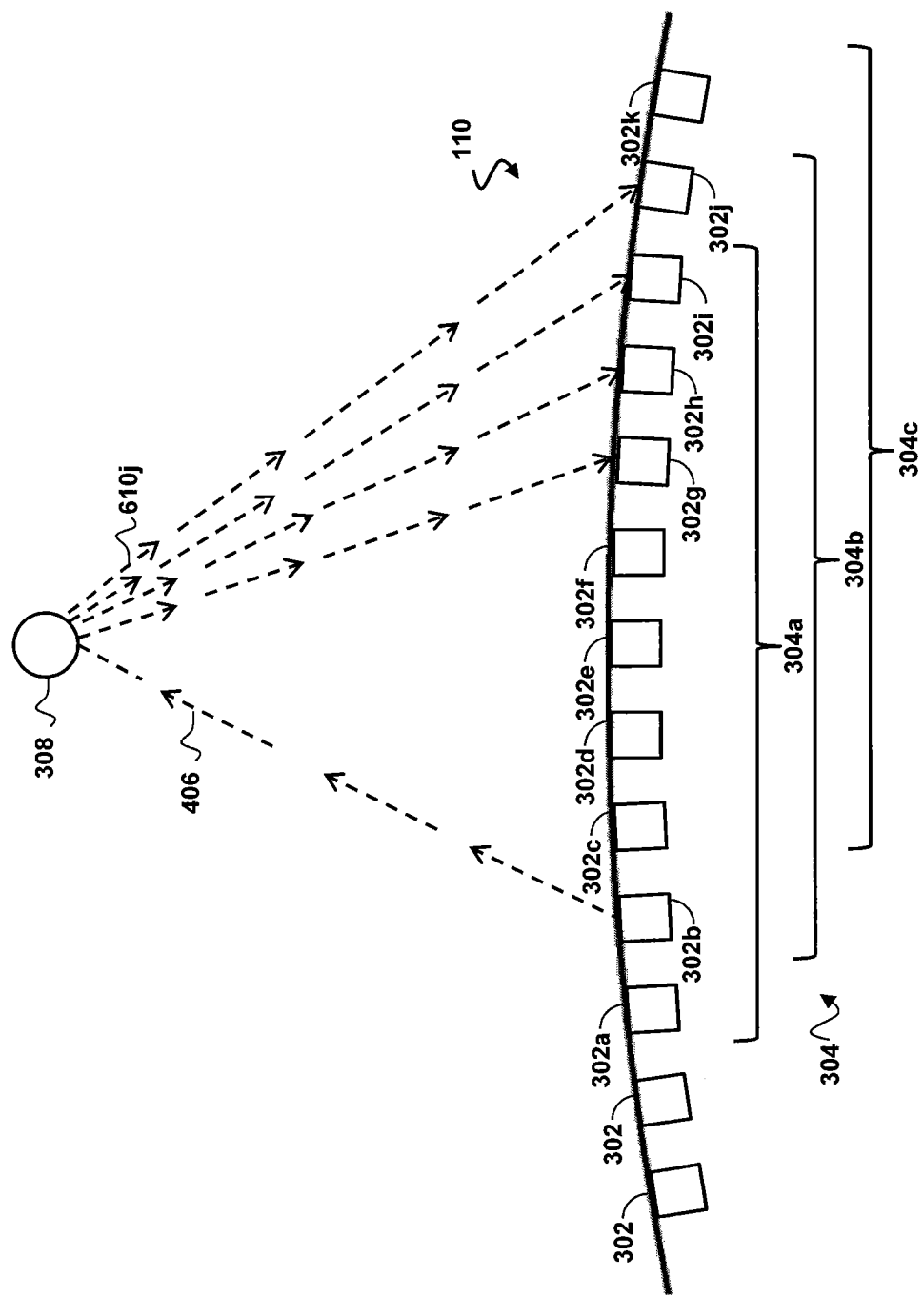
FIG. 6 is a radial cross-sectional view of a portion of a transducer complex according to aspects of the present disclosure.

FIG. 6 is a radial cross-sectional view of a portion of a transducer complex 110 according to aspects of the present disclosure. In some embodiments, data collection is expedited by collecting data for multiple apertures 304 simultaneously. As previously noted, each transducer may be part of more than one aperture, and accordingly, each A-line (transducer combination) may be part of more than one aperture. A-lines from transducer 302b received at transducers 302b through 302i are part of apertures 304a and 304b. A single additional A-line measurement 610j from transducer 302b to transducer 302j is sufficient to provide complete datasets for both apertures with regard to emitting transducer 302b. Accordingly, in an embodiment, the firing pattern of transducer 302b generates the data required for both apertures 304a and 304b.

Referring back to FIG. 5, the first exemplary nine-transducer aperture includes transducers $T_A$ through $T_I$, as indicated by triangle 502a. A second adjacent aperture includes transducers $T_B$ through $T_J$ as indicated by triangle 502b. Accordingly, in an embodiment, during the receive cycle of emitting transducer $T_B$, an additional firing is performed for receiving transducer $T_J$. This produces data for the first and second apertures 502a and 502b. Furthermore, the receive cycle for emitting transducer $T_C$ includes receiving transducers $T_C$ through $T_K$ to produce data for the first and second apertures 502a and 502b as well as a third represented by triangle 502c. In other words, for a given aperture having N transducers and an initial transducer index of i, signals generated by transducer $T_i$ are received at each transducer between $T_i$ and $T_{i+N-1}$ inclusive. Signals generated by transducer $T_{i+1}$ are received at each transducer between $T_{i+1}$ and $T_{i+N}$ inclusive, despite the fact that $T_{i+N}$ is not included in the first aperture. The sequence continues until the full dataset for the given aperture has been collected, at which time partial data will have been collected for N−1 other apertures. Some embodiments take advantage of concurrent collection of data pertaining to multiple apertures to perform aperture processing in parallel. As an example, signal data for transducer $T_c$ is used in apertures 502a, 502b, and 502c. Thus, in some embodiments, the signal data for transducer $T_c$ may be processed for apertures 502a, 502b, and 502c concurrently.

FIG. 7 is a flow diagram of a method 700 of collecting ultrasound data for multiple apertures 304 concurrently according to aspects of the present disclosure. It is understood that additional steps can be provided before, during, and after the steps of method 700, and some of the steps described can be replaced or eliminated for other embodiments of the method 700. Referring to block 702, an aperture 304 and the associated transducers 302 within the aperture are identified. This may include identifying transducers located at each end of the aperture. In block 704, initial emitting and receiving transducers are designated. In one embodiment, a transducer at an end of the aperture is designated as both the first emitting and the first receiving transducer. In block 706, the designated emitting transducer or transducers are triggered to emit ultrasonic energy. In block 708, the designated receiving transducer or transducers receive the reflected ultrasonic echo and convert the received energy into echo data. In block 710, the echo data is provided for processing in multiple apertures, such as the apertures that contain the designated transducers.

In block 712, it is determined whether a designated receiving transducer is the final transducer in the walk pattern. If the receiving transducer is not the final transducer in the walk pattern, in block 714, the next receiving transducer or transducers are designated according to the pattern. In some such embodiments, advancing in a first direction is designated as a forward walk, while advancing in a second direction is designated as a backward walk. The transmit and receive sequence of blocks 706 and 708 is repeated using the newly designated transmitter and receiver group.

If, in block 712, the receiving transducer is the final transducer in the pattern, the receive cycle is completed for the emitting transducer. Upon completion of the receive cycle, the method proceeds from block 712 to block 716 where it is determined whether a current emitting transducer is the final transducer in the emitter walk pattern. If not, in block 718, the next emitting transducer or transducers are designated. In block 718, the next receiving transducer or transducers may be designated as well, according to the receiver walk pattern. In some embodiments, in block 720, the walk pattern is modified (e.g., alternated between a forward walk and a backward walk). The method then proceeds to block 714.

The method 700 continues until the final emitting transducer of an aperture has completed a receive cycle. When this occurs, the method 700 proceeds from block 716 to block 722, where the focused A-line data for the aperture is transmitted. The method 700 then proceeds to block 718, where the emitting and receiving transducers are incremented and data collection is performed for subsequent apertures. Even where this data collection method does not improve the time to collect the first aperture dataset, it may reduce the time required to obtain the subsequent aperture datasets because of the concurrent collection of data pertaining to multiple apertures.

It is understood that disclosing the method 700 in terms of stepping through receiving transducer for a designated emitting transducer is purely arbitrary. In some embodiments, a receiving transducer is designated and the method 700 proceeds through a sequence of emitting transducers before designating a new receiving transducer. Furthermore, the walk patterns disclosed are examples selected for clarity of illustration. Other walk patterns are contemplated and provided for.

FIG. 8 is a plot of received transducer echo data 802 over time according to aspects of the present disclosure. In many embodiments, analog transducer echo data 802 is digitized for further processing in a digital domain. Digitization often includes taking samples of the analog data at discrete points in time as indicated by lines 804. This digitization may be performed within an IVUS device 102, within a PIM 104, within an IVUS processing system 106, and/or at another suitable location within another IVUS component. In some embodiments, digitization is performed using a fixed-clock-rate digitizer. This produces a fixed number of digital samples per increment of time. However, memory, processing resources, and processing time may be reduced by sampling echo data frequently during a period when echo data is expected to arrive at the receiving transducer and less frequently or not at all elsewhere. Thus, in some embodiments, digitization is performed using a variable-frequency digitizer. This may reduce the number of samples in the digitized echo data and may reduce the system requirements to process the echo data.

Referring to FIG. 8, a sampling pattern for the echo data may contain an initial period 806 when the signal produced by a receiving transducer is not relevant. Accordingly, samples during the initial period 806 may be omitted. For example, this initial period 806 may correspond to a time when the reflection of the ultrasonic emission has not yet arrived, and therefore any measurement is background noise. The sampling pattern may also contain one or more active periods 808 and 810 when the echo data 802 is sampled at a varying frequencies. In an embodiment, during a first active period 808 when the signal data is less relevant, the data is sampled at a relatively lower frequency than during a second active period 810. Many factors may affect data relevance. For example, periods corresponding to a focal range outside of a range of interest may be of less relevance. As a further example, periods corresponding to data produced before the emitter reaches peak output may exhibit a reduced signal-to-noise ratio and thus be less relevant. The sampling pattern may account for these relevance factors and others. In various embodiments, the timing and duration of the active periods 808 and 810 as well as the sampling rates during the active periods are selected to balance sample size and data quality.

Variable-frequency sampling can be performed utilizing a variable-frequency oscillator. In such embodiments, the simplicity of the digitizer design must be balanced against possible drawbacks. For example, variable-frequency oscillators may require complicated control logic, may require more power than fixed-frequency oscillators, may generate more heat than fixed-frequency oscillators, and may have reduced reliability.

FIGS. 9a and 9b are schematic diagrams of variable-clock-rate digitizers according to aspects of the present disclosure. The digitizer 900 of FIG. 9a incorporates a fixed-rate oscillator 902 and a bump map generator 904. The digitizer 900 receives analog echo data 906 alone or in conjunction with a transducer configuration 908 of the A-line used to produce the echo data 906. For example, the transducer configuration 908 may indicate the A-line or emitter/receiver pair that generated the echo data 906. From the transducer configuration 908, the bump map generator 904 determines a sampling pattern for echo data.

The sampling pattern may be based on a geometry of a transducer complex 110 (e.g., degree of curvature, transducer spacing, distance between emitter and receiver, length of signal lines, etc.), a characteristic of a transducer (e.g., firing delay, sensitivity etc.), a characteristic of an aperture (e.g., width, location on the transducer complex, etc.), and/or other relevant factors that affect arrival time, signal quality, signal relevance, etc. In an exemplary embodiment, A-lines having a single transducer acting as both emitter and receiver may have a shorter distance to and from a target structure than transducer pairs spaced further apart. The sampling pattern may be structured accordingly. In another exemplary embodiment, the sampling pattern accounts for manufacturing variances. In various other embodiments, the temporal location of the sampling pattern accounts for other effects, both measured and calculated, that affect the time at which the echo data is received.

In some embodiments, the total number of samples is determined by a reference A-line. In one such embodiment, the bump map for a reference A-line specifies a total of 3000 samples. In the embodiment, bump maps for other related A-lines specify the same number of total samples, although the arrangement in time may vary.

The sampling pattern can be used to align echo data 906 collected from various A-lines within an aperture. In some embodiments, this is performed by selecting the periods of the sampling pattern including the initial period 806 to perform the temporal alignment of echo data 906 between A-lines. In some embodiments, the sample rates of the periods of the sampling pattern are calculated to perform the temporal alignment of echo data.

The bump map generator 904 creates a bump map 910 corresponding to the sampling pattern. In some embodiments, the bump map 910 includes a binary data (0s and 1s) where a 1 indicates that a sample of the analog data should be taken at the corresponding clock pulse and a 0 indicates that a new sample should not be taken at the corresponding clock pulse. In alternate embodiments, a 1 indicates that a new sample should not be taken at the corresponding clock pulse and vice versa.

The bump map 910 and the clock produced by the fixed-rate oscillator 902 are provided to the analog-to-digital converter 912. The analog-to-digital converter 912 samples the analog echo data at the clock rate determined by the combination of the clock and the bump map 910. In some embodiments, the bump map 910 masks the clock. For example, the bump map 910 and the clock may be supplied as inputs to an AND-gate within the analog-to-digital converter 912. The output of the AND-gate can serve as sample clock used to by the analog-to-digital converter 912 to sample the analog echo data. In this way, the analog-to-digital converter 912 produces digitized echo data 914 from the analog echo data 906 having a sample frequency determined by the combination of the clock and the bump map 910.

The digitizer 950 of FIG. 9*b* also incorporates a fixed-rate oscillator 902 and a bump map 910. Digitizer 950 is substantially similar to digitizer 900, except as noted. One distinction is that the digitizer 950 incorporates an analog-to-digital converter 912 that samples at a fixed frequency based on the clock generated by the fixed-rate oscillator 902. As with a fixed-rate oscillator, a fixed-frequency analog-to-digital converter may be less complicated, may consume less energy, may generate less heat, and/or may be more reliable than a variable-rate alternative. Accordingly, digitizer 950 may have reduced size, complexity, and/or power consumption, and may have improved reliability compared to alternative designs.

The analog-to-digital converter 912 produces fixed-rate digitized echo data 952, which is converted to variable-rate digitized data 956 by a rate converter 954 according to the bump map 910. In doing so, the rate converter 954 may perform downsampling, upsampling, interpolation, and/or other modifications to the fixed-rate data 952. Accordingly, in some embodiments, the rate converter 954 discards samples from the fixed-rate digitized echo data 952 to produce the variable-rate digitized echo data 956. In some embodiments, the rate converter resamples and thereby adds samples to the fixed-rate digitized echo data 952. In some embodiments, the rate converter interpolates values from samples of the fixed-rate digitized echo data 952 to produce the variable-rate digitized echo data 956.

FIG. 10 is a flow diagram of a method 1000 of generating variable-rate digitized ultrasound data according to aspects of the present disclosure. It is understood that additional steps can be provided before, during, and after the steps of method 1000, and some of the steps described can be replaced or eliminated for other embodiments of the method 1000. Referring to block 1002, analog echo data is received from an A-line transducer group. The analog echo data may be received directly from the transducers 302 of the A-line or from an amplifier, a filter, a signal conditioner, and/or other suitable interface system. In block 1004, a fixed frequency reference clock is received. The frequency of the reference clock may correspond to a maximum sampling frequency to be used during the generation of the variable-rate digitized data. In block 1006, a transducer configuration is received that specifies some aspect of the A-line. The transducer configuration may specify the transducers of the A-line, a geometry of a transducer complex 110, a characteristic of a transducer, a characteristic of an aperture, and/or other relevant factors from which temporal characteristics of the echo data can be determined.

In block 1008, a bump map is determined from the transducer configuration. The bump map specifies the sampling intervals of the digitized echo data, and may be used to specify an initial interval during which the analog echo data is not sampled, active intervals during which the echo data is sampled at a reduced frequency, active intervals during which the echo data is sampled at an increased frequency, and other critical time intervals.

In some embodiments, the intervals are selected to provide an increased sampling rate during a period where echo data is expected. By reducing the number of samples elsewhere, the bump map may reduce the memory, processing resources, clock speeds, and power consumption used for data handling and focusing. In some embodiments, the bump map coordinates the total number of samples between multiple A-lines. For example, the total samples may be set by a reference A-line, and bump maps for other A-lines in the aperture may conform to the reference total. In some embodiments, the bump map is used to perform a temporal alignment of echo data across A-lines.

In some embodiments, the bump map includes a sequence of binary data (0s and 1s) where a 1 indicates that a sample of the analog data should be taken at the corresponding clock pulse and a 0 indicates that a new sample should not be taken at the corresponding clock pulse. In alternate embodiments, a 1 indicates that a new sample should not be taken at the corresponding clock pulse.

In block 1010, the analog echo data is digitized according to the reference clock and the bump map to produce the variable-rate digital echo data. In some embodiments, the bump map is used to gate the reference clock and produce a variable-rate clock for sampling. In further embodiments, the analog data is first digitized by sampling at the reference clock frequency, and the fixed-frequency data is downsampled, upsampled, interpolated, and/or otherwise modified according to the bump map. Utilizing a bump map allows the digital echo dataset to be reduced without adversely affecting data quality and without the use of variable-frequency devices that may require complicated control logic, may require more power than fixed-frequency equivalents, and may demonstrate reduced reliability.

FIG. 11 is a cross-sectional view of a focused aperture 304 of a transducer complex 110 according to aspects of the present disclosure. Once the aperture data is collected, it may undergo a mathematical focusing process. Focusing improves image quality by adjusting and combining data collected from the A-line transducer combinations. The effect of focusing is to combine the A-line data into a dataset that simulates a narrow-width emission from a location within the aperture 304 and received at a location on the transducer complex 110, regardless of whether transducers 302 actually exist at these locations or whether such a narrow-width emission could be produced. In some embodiments, more than one focused A-line is produced per aperture 304. The different focused A-lines may be directed at different angles from the surface of the transducer complex 110. For example, focusing may produce data for A-lines 1102a, 1102b, and 1102c. These different focused A-lines may be referred to as different flavors of focused A-line data. In some embodiments, the focusing calculations are range sensitive. For example, a given focused A-line (e.g., A-line 1102a) may be calculated using one set of factors for range 1104a, another set for 1104b, and another for 1104c. In further non-limiting examples, a given focused A-line is calculated for other numbers of ranges 1104 including 2, 4, 5, 6 and 9. In an embodiment, the number of ranges 1104 is the number of samples collected for a measured (not focused) A-line. Other suitable numbers of ranges are provided for. Thus, focusing may include sets of calculations divided by range, flavor, and/or other aspects of the focused A-line to be produced.

The process of focusing may include space-time alignment of data (radial focusing, a radial direction indicated by arrow 1106) as well as spatial alignment of data (azimuthal focusing, an azimuthal direction indicated by arrow 1108). The first type of alignment, space-time alignment, may include time-of-flight adjustment. Due to different flight paths between A-lines, received echoes may arrive at the transducers at different times. Time-of-flight adjustment shifts the received responses in time to align the signals with those of other A-lines within the aperture. The second type of alignment, spatial alignment may include amplitude balancing and apodization. One type of amplitude balancing applies an amplitude adjustment to the received responses based on characteristics of the transducers. For example, a transducer may have reduced sensitivity to signals directed at oblique angles. Thus, a directional amplification factor may be determined based on the receiving transducer's location relative to the emitting transducer. In a further example, an adjustment may be applied to correct for a less-sensitive transducer such as one that may result from a manufacturing variance. Apodization is another type of amplitude weighting and may be used to reduce grating and side lobe effects and other artifacts from the imaging process. Apodization may include tapering off the amplitude of a received response on either side of a window of time. This emphasizes the response during the peak of the window. Exemplary apodization weightings include boxcar, Hann, Hamming, cosine, root-raised-cosine, and half-cosine window functions.

Figure 12:
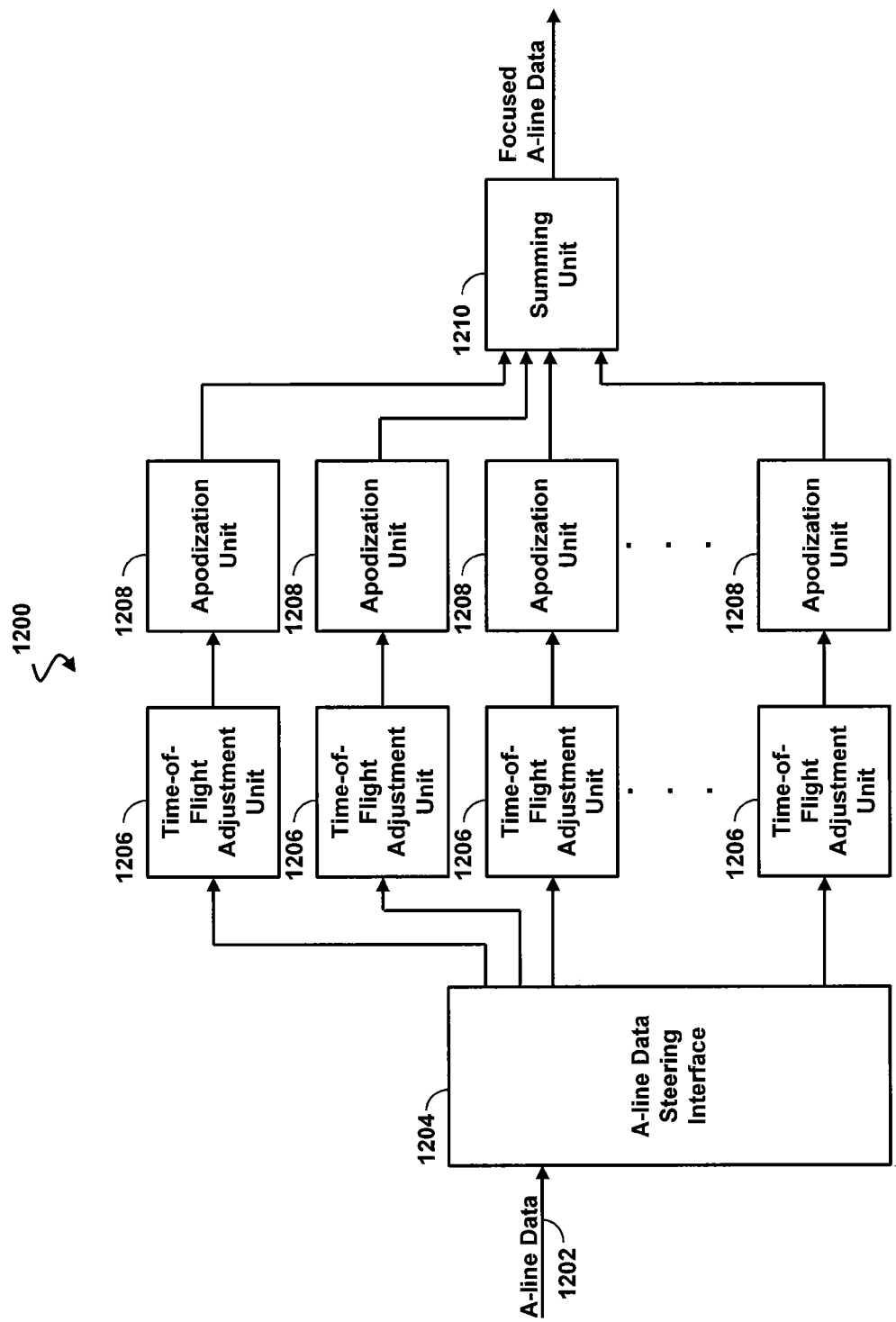
FIG. 12 is a schematic of a focusing system according to aspects of the present disclosure.

FIG. 12 is a schematic of a focusing system 1200 according to aspects of the present disclosure. Portions of the focusing system 1200 may be incorporated into an IVUS processing system 106, a patient interface monitor (PIM) 104, and/or other components of an IVUS imaging system 100. In various embodiments, the focusing system 1200 focuses A-line data from the transducers 302 within an aperture 304 to produce a focused dataset for the aperture 304. Focusing system 1200 receives A-line data 1202 via an A-line data steering interface 1204. In some embodiments, the interface 1204 receives the A-line data 1202 from a transducer complex 110. In some such embodiments, the A-line interface 1204 receives data directly from transducers 302 of the transducer complex 110. In some embodiments, the A-line interface 1204 receives data from a memory subsystem such as a data buffer, an analog-to-digital converter, an analog and/or digital amplifier, a filter, a signal conditioner, and/or other suitable interface systems. The A-line data steering interface 1204 directs the received data to the appropriate time-of-flight (TOF) adjustment unit 1206.

The time-of-flight adjustment units 1206 align the A-line data in time. In the illustrated embodiment, the focusing system 1200 includes a time-of-flight adjustment unit 1206 for each A-line in the aperture, although only four are illustrated for the sake of clarity. Other embodiments incorporate as few as one time-of-flight adjustment unit 1206. The time-of-flight adjustment unit or units 1206 align the A-line data by shifting the signal in time according to an offset. In some embodiments, the particular offsets applied by the units 1206 are determined based on a geometry of the transducer complex 110 (e.g., degree of curvature, transducer spacing, distance between emitter and receiver, length of signal lines, etc.), a characteristic of a transducer (e.g., firing delay, sensitivity etc.), a characteristic of an aperture (e.g., width, location on the transducer complex, etc.), and/or other relevant factors that affect arrival time. In some embodiments, such as when a focused A-line is broken up into more than one calculation based on a distance range 1104 or flavor, discrete time-of-flight offsets are supplied for each particular focal range 1104 or flavor. In some embodiments, time-of-flight offsets are determined by analysis of the incoming A-line data through a method such as peak detection either in addition to or as a replacement for utilizing pre-determined values. After the offset is applied, the aligned A-line data is supplied to the apodization units 1208.

Apodization units 1208 apply a set of amplitude weightings to correct for grating and side lobe effects. Such weighting typically taper off the amplitude of a received response on either side of a window of time and may be derived from apodization functions such as a boxcar, Hann, Hamming, cosine, root-raised-cosine, half-cosine window function and/or other suitable apodization function. The apodization units 1208 may also perform an amplitude adjustment based on transducer characteristics. For example, the amplitude adjustment may correct for a transducer with reduced sensitivity. The resulting aligned and apodized data is provided to a summing unit 1210, which adds the data from the unfocused A-lines to produce focused A-line data for the aperture.

Figure 13:
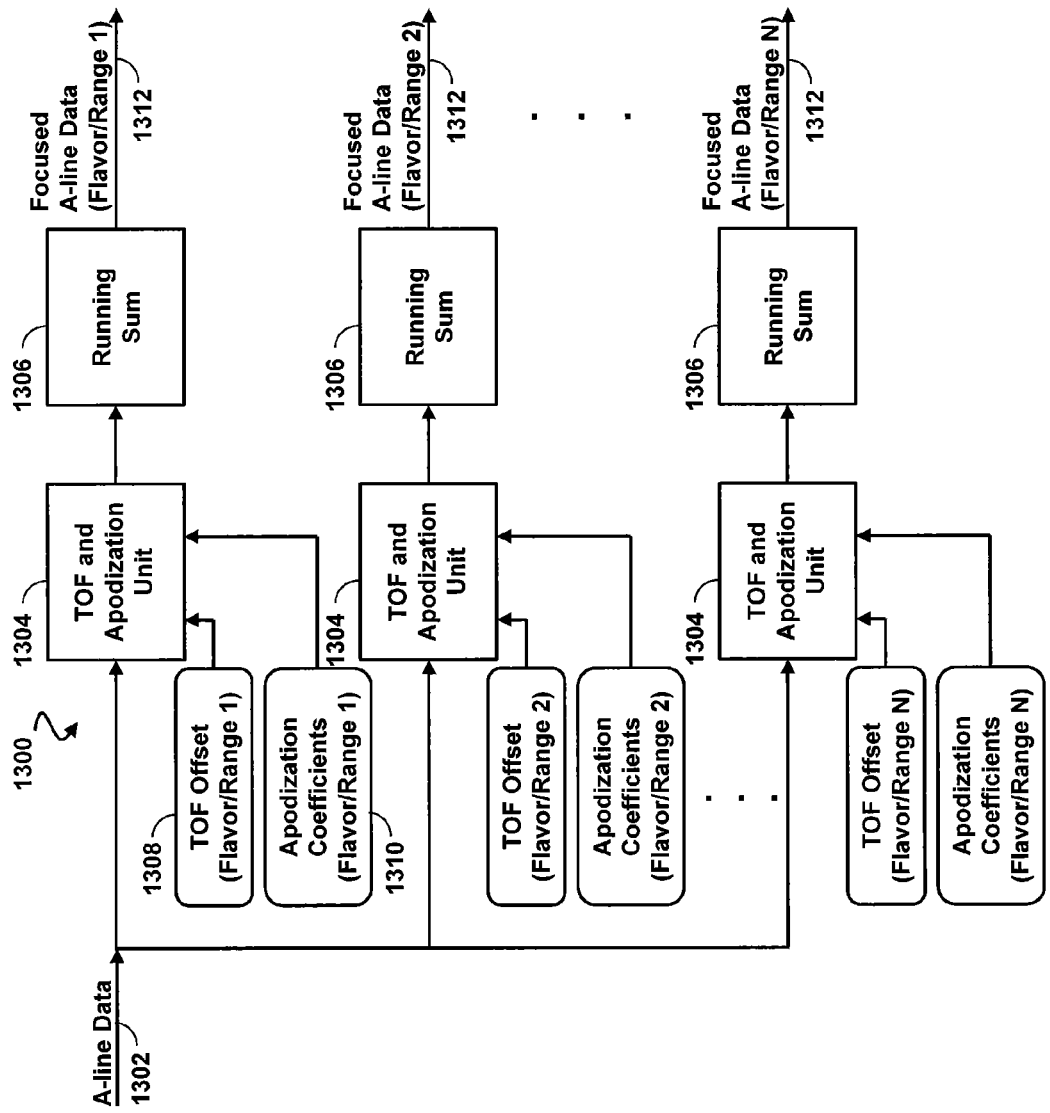
FIG. 13 is a schematic of an aperture engine according to aspects of the present disclosure.

FIG. 13 is a schematic of an aperture engine 1300 according to aspects of the present disclosure. Portions of the aperture engine 1300 may be incorporated into an IVUS processing system 106, a patient interface monitor (PIM) 104, and/or other components of an IVUS imaging system 100. In some embodiments, the aperture engine 1300 leverages the parallel nature of the focusing calculations to improve focusing throughput. In contrast to focusing system 1200, aperture engine 1300 incorporates a running sum unit 1306 and a streamlined interface in combination with a parallelized architecture. In the illustrated embodiment, the aperture engine 1300 performs N parallel calculations of focused A-line data, of which three are shown. Further embodiments incorporate other numbers of TOF and apodization units 1304 and running sum units 1306 to produce other number of flavors. For example, in one such embodiment, the aperture engine 1300 includes a single TOF and apodization unit 1304 and a single running sum unit 1306.

The aperture engine 1300 receives raw A-line data for focusing. This data may be received from a transducer complex 110, a memory subsystem, an analog-to-digital converter, an analog and/or digital amplifier, a filter, a signal conditioner, and/or other suitable interface systems. The received A-line data 1302 is then distributed to one or more time-of-flight (TOF) and apodization units 1304. In the illustrated embodiment, each unit 1304 corresponds to a subset of focused A-line data. In various examples, the subsets are divided by range and/or flavor, although obviously other divisions are provided for. Each TOF and apodization unit 1304 receives a set of TOF adjustments 1308 and apodization coefficients 1310. The values of the TOF adjustments 1308 and apodization coefficients 1310 within the set may be determined based on the subset of focused A-line data assigned to the TOF and apodization unit 1304. For example, a first set of TOF adjustments 1308 and apodization coefficients 1310 may be correspond to a first flavor and range combination. The units 1304 may then align the A-line data samples in time according to the TOF adjustment factors 1308 and may apply an apodization function and/or amplitude balancing according to the apodization coefficients 1310.

The aligned and apodized A-line data produced by the one or more TOF and apodization units 1304 is input into a corresponding running sum unit 1306. The running sum unit 1306 adds the aligned and apodized data for the A-lines that make up the aperture. When the running sum unit 1306 has accumulated sufficient data, the unit 1306 produces the focused A-line data 1312. This data 1312 may be a subset (e.g., select flavors and/or ranges) of the total focused A-line data for the aperture. By providing multiple TOF and apodization units 1304 and running sum units 1306, the aperture engine 1300 is thus able to produce multiple subsets of data 1312 concurrently.

In addition to the advantages of parallelization, another advantage to this architecture is that, in some embodiments, the A-line data is distributed to any number of TOF and apodization units 1304 without a data steering interface. This streamlined interface may allow the circuitry for generating each data subset (including the associated TOF and apodization unit 1304 and running sum unit 1306) to be implemented on a separate computing hardware device (e.g., a general purpose processor, a graphic processing unit, an ASIC, an FPGA, a DSP, a microcontroller, etc.). In the alternative, in some embodiments, the circuitry for calculating multiple data subsets is implemented on a single computing hardware device. Furthermore, in some embodiments, the elimination of steering circuitry allows the complete aperture engine 1300 to be implemented on a single computing hardware device. In this way, the present disclosure provides a scalable aperture engine 1300 capable of producing focused A-line datasets corresponding to multiple flavors, ranges, or other division simultaneously, and provides an efficient interface that allows for single-chip as well as multiple-chip implementations.

Figure 14:
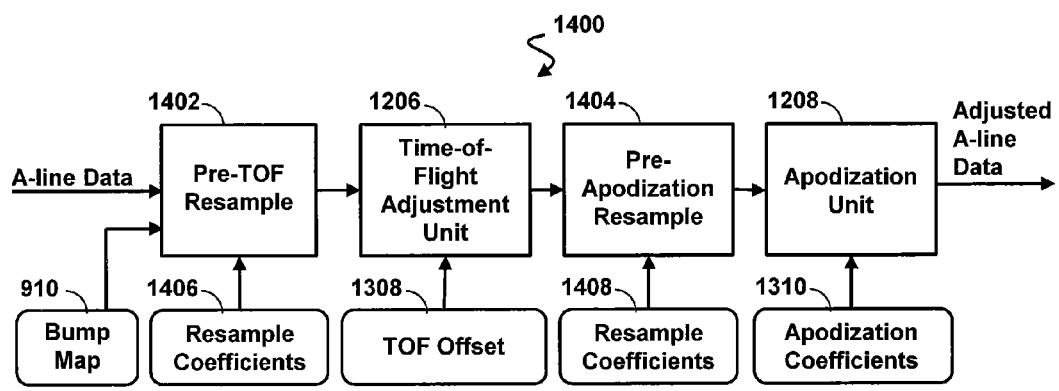
FIG. 14 is a schematic of a TOF and apodization unit according to aspects of the present disclosure.

FIG. 14 is a schematic of a TOF and apodization unit 1400 according to aspects of the present disclosure. The TOF and apodization unit 1400 is suitable for use in an aperture engine 1300 such as that disclosed with reference to FIG. 13. The TOF and apodization unit 1400 includes a time-of-flight adjustment unit 1206 and an apodization unit 1208 substantially similar to those described with reference to FIG. 12. The TOF and apodization unit may also include a pre-TOF resample unit 1402 and/or a pre-apodization resample unit 1404. In various embodiments, the resample units 1402 and 1404 are used to condition data by upsampling and/or downsampling.

The pre-TOF resample unit 1402 may perform the variable rate digitization and/or the variable-rate conversion of the A-line data disclosed with reference to FIG. 9. In such embodiments, the pre-TOF resample unit 1402 may receive a bump map 910 that designates a sampling pattern. The sampling pattern may be based on a geometry of a transducer complex 110 (e.g., degree of curvature, transducer spacing, distance between emitter and receiver, length of signal lines, etc.), a characteristic of a transducer (e.g., firing delay, sensitivity etc.), a characteristic of an aperture (e.g., width, location on the transducer complex, etc.), and/or other relevant factors that affect arrival time, signal quality, signal relevance, etc. The total number of samples in the sampling pattern may be determined based on a reference A-line. For example, bump maps for related A-lines may designate sampling patterns having the same number of total samples, although the arrangement in time may vary. The sampling pattern may also align echo data collected from various A-lines within an aperture. As an alternative to receiving a bump map 910 that designates the sampling pattern, the pre-TOF resample unit 1402 may receive parameters used to determine the bump map 910.

In some embodiments, the pre-TOF resample unit 1402 is used to improve the accuracy of the time-of-flight adjustment by increasing the effective sample rate of the A-line data. Resampling achieves some of the benefits of a higher sampling rate without the extensive hardware requirements associated with higher data rates. The pre-TOF resample unit 1402 may also be used to apply a time-of-flight adjustment either in addition to or as a replacement for the adjustment applied in the TOF adjustment unit 1206.

In an exemplary embodiment, A-line data sampled at 200 megasamples/sec is received at the pre-TOF resample unit 1402. The pre-TOF resample unit 1402 resamples the A-line data at 4× thereby providing A-line data sampled at 800 megasamples/sec to the TOF adjustment unit 1206. Any suitable resampling algorithm including any suitable resampling filter may be used to resample the data. Resampling algorithms are known to those of skill in the art. Non-limiting examples of resampling algorithms include linear interpolation, Lagrange interpolation, cubic spline interpolation, polyphase interpolation, and/or other suitable algorithms. In some such embodiments, the pre-TOF resample unit 1402 receives a set of resample coefficients 1406 specifying a resampling rate, coefficients for a resampling algorithm, and/or other resampling configuration data.

As an alternative to performing a full upsample of the A-line data, in some embodiments, the pre-TOF resample unit 1402 performs an interpolated phase shift. An interpolated phase shift produces output data at the same sample rate as the input data, but time shifted so that the samples corresponds to shifted points in time. For example, a 4× interpolated phase shift may produce phase shifts of 0°, 90°, 180°, and 270°. Given input A-line data with samples at integer values of time (e.g., 1, 2, 3, 4, 5, 6, etc.), a phase shift of 90° would produce output A-line data at the same sample rate but with samples corresponding to amplitude values at times 1.25, 2.25, 3.25, 4.25, etc. These intermediate amplitude values may be calculated using any suitable resampling algorithm. A phase shift of 180° would produce output A-line data at the same sample rate but with samples corresponding to amplitude values at 1.5, 2.5, 3.5, 4.5, etc. A phase shift of 270° would produce output A-line data corresponding to values at 1.75, 2.75, 3.75, 4.75, etc. This phase shift provides increased data granularity without the higher data rate. To provide further data granularity, a phase shift sequence, such as (180°, 90°, 0°, 270°, 180°, 0°), may be used to produce output A-line data at the same sample rate as the input but with samples corresponding to amplitude values at times, such as 1.5, 2.25, 3, 4.75, 5.5, 6, etc.

In various embodiments, interpolation retains the benefits of the lower bit-rates such as lower clock frequencies, reduced data steering, decreased circuit complexity, and/or reduced memory requirements. Furthermore, as can be seen, this phase shift may be incorporated as part of the time-of-flight adjustment. In some embodiments and for some A-line configurations, this phase shift may suffice to align the data such that no further time-of-flight adjustment is needed. Another advantage is that some embodiments, certain focusing steps benefit from increased data granularity while others do not. Accordingly, performing a single interpolated phase shift may avoid an upsampling process followed by a downsampling process.

To provide further data granularity, in some embodiments, the phase shift may vary for each sample. For example, a phase shift sequence (180°, 90°, 0°, 270°, 180°, 0°) may be used to produce output A-line data at the same sample rate as the input but with samples corresponding to amplitude values at times 1.5, 2.25, 3, 4.75, 5.5, 6.

In various embodiments, the pre-TOF resample unit 1402 receives a set of resample coefficients 1406 specifying a resample rate, specifying a phase shift, specifying coefficients for an interpolation algorithm, and/or specifying other resampling configuration data. In some embodiments, the pre-TOF resample unit 1402 performs the fixed-to-variable rate echo data conversion described with reference to FIGS. 9a and 9b. In such embodiments, the resample coefficients 1402 may include a bump map 910 and/or configuration data from which a bump map 910 may be determined.

The pre-apodization resample unit 1404 may perform an upsampling and/or an interpolated phase shift substantially similar to that described with respect to the pre-TOF resample unit 1402. Alternatively, in some embodiments, the pre-apodization resample unit 1404 performs a downsampling of the time-of-flight adjusted echo data. Whereas focusing may benefit from increased accuracy created by interpolation, apodization and weighting may not. In some embodiments, apodization accuracy is not improved for any sample rate beyond a threshold based in part on the resolution of the final image.

Figure 15:
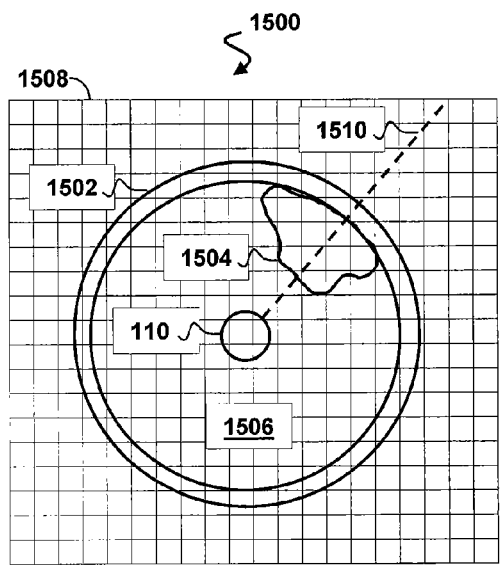
FIG. 15 is an illustration of an ultrasound image produced by an intravascular ultrasound imaging system according to aspects of the present disclosure.

FIG. 15 is an illustration of an ultrasound image 1500 produced by an intravascular ultrasound imaging system 100 according to aspects of the present disclosure. From image 1500 a skilled operator can identify structures including the transducer complex 110, borders of a vessel 1502, a plaque 1504, blood 1506, and/or other structures of interest. Digital images including image 1500 are comprised of a set of pixels 1508 (enlarged for clarity). As pixels 1508 are areas of uniform color and intensity, data beyond an amount needed to determine color and/or intensity for a pixel can be discarded without affecting the final image 1500. For a hypothetical A-line (e.g., the A-line represented by dashed line 1510), it can be determined how many pixels 1508 are intersected and accordingly how many samples are needed. In some embodiments, the sampling rate is determined based on a ratio of samples per pixel. In one such embodiment, A-line data is sampled at a rate of one sample per pixel. Sampling based on a ratio of samples per pixel may be referred to as per-pixel resampling or pixel-aware resampling. Omitting samples that have no effect on the final image per-pixel resampling may allow a reduction in computing hardware, for example the apodization unit 1208, as the dataset being manipulated is smaller. This can result in improved efficiency, reduced system size, and reduced cost. In an embodiment, per-pixel resampling allows a mid-range imaging system to produce a high-resolution image such one configured for a high-definition display.

As the image 1500 is a Cartesian representation of a polar dataset, the intersections of the A-lines and the pixels may be calculated or a set of Cartesian and/or polar approximations may be used. Cartesian approximations may rely on trigonometric principles to determine a unique number of samples for each A-line based on the angle. A-lines directed perpendicular to a row or column of pixels (e.g., horizontal and vertical A-lines) will intersect the fewest number of pixels, whereas A-lines directed at 45° to a perpendicular A-line can be assumed to intersect the most. Accordingly, in some embodiments using a Cartesian approximation, perpendicular A-lines will be resampled to have a first number of samples while the number of samples for other A-lines will be based on an angle relative to a perpendicular A-line. In an exemplary polar approximation, each focused A-line is resampled at the same number of samples. The particular number of samples is determined by an archetypal A-line. The archetypal A-line may be an A-line having the most intersections, an average (mean or median) number of intersections, or other suitable number of intersections. These exemplary approximations are not limiting, and embodiments utilizing other suitable approximations are contemplated and provided for. For example, in some embodiments, an area-based approximation apportions the total number of pixels for the image 1500 among the A-lines, where the number of samples per A-line corresponds to the total number of pixels in the image divided by the total number of focused A-lines.

In some embodiments, the pixel-to-sample relationship is reevaluated when operating parameters change. For example, increasing the field-of-view may increase the number of samples per image while the number of pixels in the image remains the same. Accordingly, the pixel-to-sample ratio may be recalculated as field-of-view changes. Other operating parameters may affect the number of samples collected or focused, the resolution of the image, and/or the target sample-to-pixel ratio.

Figure 16:
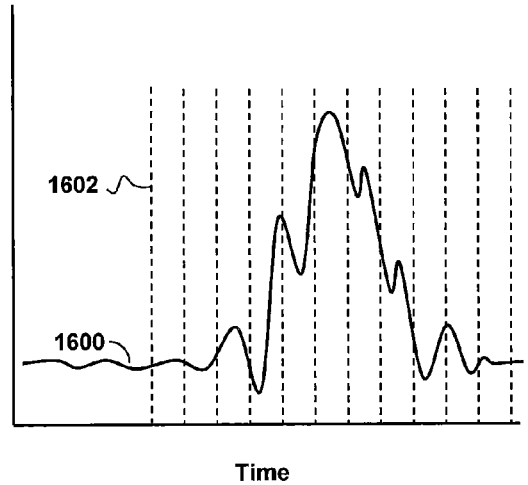
FIG. 16 is a plot of received transducer echo data over time according to aspects of the present disclosure.

FIG. 16 is a plot of received transducer echo data 1600 over time according to aspects of the present disclosure. The transducer echo data 1600 is sampled at discrete points in time as indicated by lines 1602. This digitization may be performed within an IVUS device 102, within a PIM 104, within an IVUS processing system 106, and/or at another suitable location within another IVUS component. In the illustrated embodiment, the points in time 1602 are determined based on a resolution of a final image. For example, the points in time 1602 are determined based on a ratio of samples per pixel such as 1:1. In some embodiments, the samples are not at fixed intervals and instead correspond to an alignment of an A-line relative to one or more pixels.

Referring again to FIG. 14, in an embodiment, the pre-apodization resample unit 1404 receives a set of resample coefficients 1408, which may include a resampling rate, interpolation coefficients, a phase adjust, a number of samples, an image or display resolution, a ratio of samples per pixel, and/or other resampling configuration data. The pre-apodization resample unit 1404 resamples the time-of-flight adjusted data according to the resample coefficients 1408 and provides the resampled data to the apodization unit 1208. The apodization unit 1208 may then perform apodization and amplitude modification on the resampled A-line data substantially as described with reference to FIG. 12, for example.

One of skill in the art will recognize that additional processing including, but not limited to, resampling may be performed on the adjusted A-line data produced by the apodization unit 1208. For example, in some embodiments, pixel-aware resampling is performed on the adjusted A-line data. This may reduce the processing required for subsequent image formation steps. As another example, in some embodiments, filtering is performed on the adjusted A-line data produced by the apodization unit 1208. Further processing steps will be known to those skilled in the art.

Figure 17:
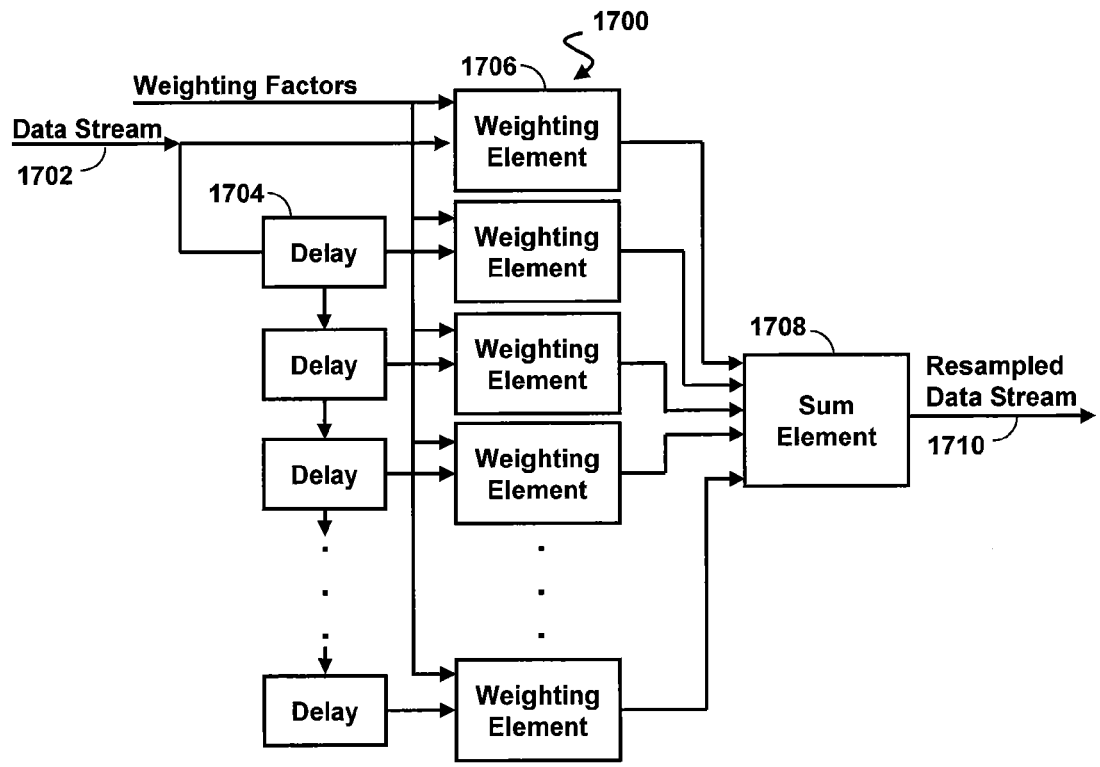
FIG. 17 is a schematic of a resampling device according to aspects of the present disclosure.

FIG. 17 is a schematic of a resampling device 1700 according to aspects of the present disclosure. The resampling device 1700 is suitable for use in a pre-time-of-flight resample unit 1402 and/or a pre-apodization resample unit 1404 such as those described with respect to FIG. 14. The illustrated resampling device 1700 is a type of polyphase interpolation device. The resampling device 1700 receives an input data stream 1702 such as a set of A-line data and distributes it through a set of delay elements 1704 to produce a set of delayed data streams. In the illustrated embodiments, the delay elements 1704 are chained to in order produce the set of delayed data. In some embodiments, chained implementations reduce the size and/or complexity of the individual delay elements 1704 that make up the network. In other embodiments, separate parallel delay elements 1704 are used to allow greater control over each delay magnitude.

Weighting elements 1706 apply weighting factors to the set of delayed data streams and the resulting weighted data streams are summed by the sum element 1708 to produce the resampled data stream 1710. The weighting factors applied by the delay elements 1706 determine the relationship of the resampled data stream 1710 and the input data stream 1702. In some embodiments, the resampling device 1700 performs a filtering function such as a bandpass, low-pass, and/or high-pass filtering. In one such embodiment, the resampling device 1700 performs a low-pass filtering by utilizing weighting factors derived from a sinc function. This is useful for eliminating high frequency noise introduced by some methods of resampling. The resampling device 1700 may also be used to perform a partial phase shift. For example, the weighting factors may be chosen to perform phase shifts of 0°, 90°, 180°, and/or 270°. In one embodiment, resampling device 1700 receives weighting factors corresponding to a phase shift selected based on a geometry of a transducer complex 110, a characteristic of a transducer, a characteristic of an aperture, and/or other relevant factors.

Figure 18:
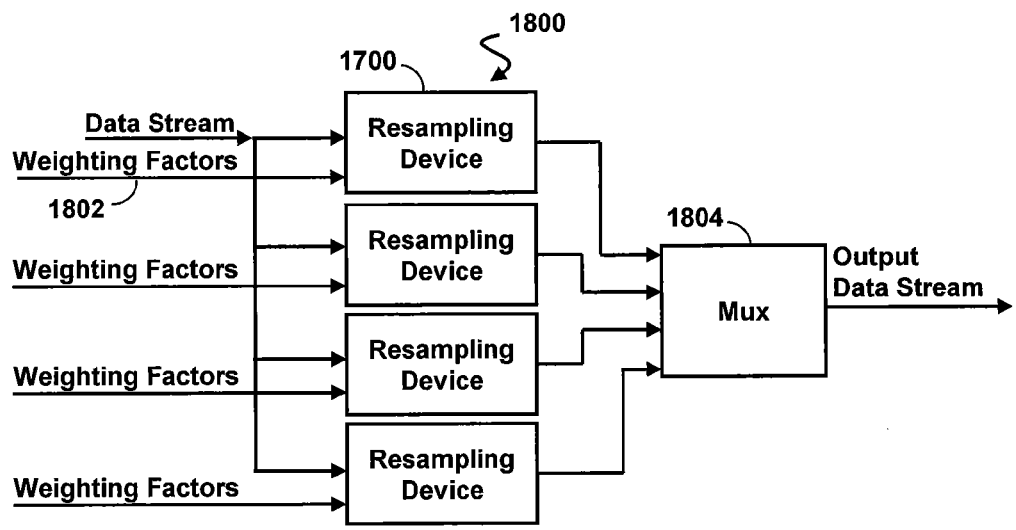
FIG. 18 is a schematic of a resampling network according to aspects of the present disclosure.

FIG. 18 is a schematic of a resampling network 1800 according to aspects of the present disclosure. The resampling network 1800 is suitable for use in a pre-time-of-flight resample unit 1402 and/or a pre-apodization resample unit 1404 such as those described with respect to FIG. 14. The resampling network 1800 may include one or more resampling devices 1700 such as the resampling device 1700 described with respect to FIG. 17. The resampling devices 1700 each receive an input data stream (for example, an input A-line data stream) and a set of weighting factors 1802. The sets of weighting factors 1802 may differ between devices 1700. The resampling network 1800 also includes a multiplexer 1804 that determines which of the resampled data streams is selected as the output data stream. In this manner, the multiplexer 1804 selects between differently weighted and resampled versions of the input data stream.

In an exemplary embodiment, a resampling network 1800 includes four resampling devices 1700. A data stream corresponding to an A-line transducer pair is received at the resampling devices 1700 along with a set of weighting factors 1802. The four sets of weighting factors correspond to phase shifts of 0°, 90°, 180°, and 270° relative to the sample period of the data stream. Accordingly, the resampling devices 1700 produce weighted resampled data streams corresponding to the four phase shifts. The multiplexer 1804 is used to select the appropriate phase shift to output based on factors such as a geometry of a transducer complex 110, a characteristic of a transducer, a characteristic of an aperture, and/or other relevant factors. In an embodiment, a phase shift sequence is supplied to the multiplexer 1804 (e.g., a sequence representing 180°, 90°, 0°, 270°, 180°, 0°), and is used by the multiplexer 1804 to produce output A-line data at the same sample rate as the input but with samples corresponding to amplitude values at times 1.5, 2.25, 3, 4.75, 5.5, 6.

Such a resampling network 1800 can perform the pre-TOF resampling described with respect to the pre-TOF resample unit 1402 of FIG. 14. By producing a phase shifted version of the input data stream having the same sampling frequency as the input data stream, the resampling network 1800 provides the greater data granularity of upsampling without increased data-handling overhead associated with higher sampling frequencies. The result is a lightweight, efficient datapath with improved data accuracy.

Figure 19:
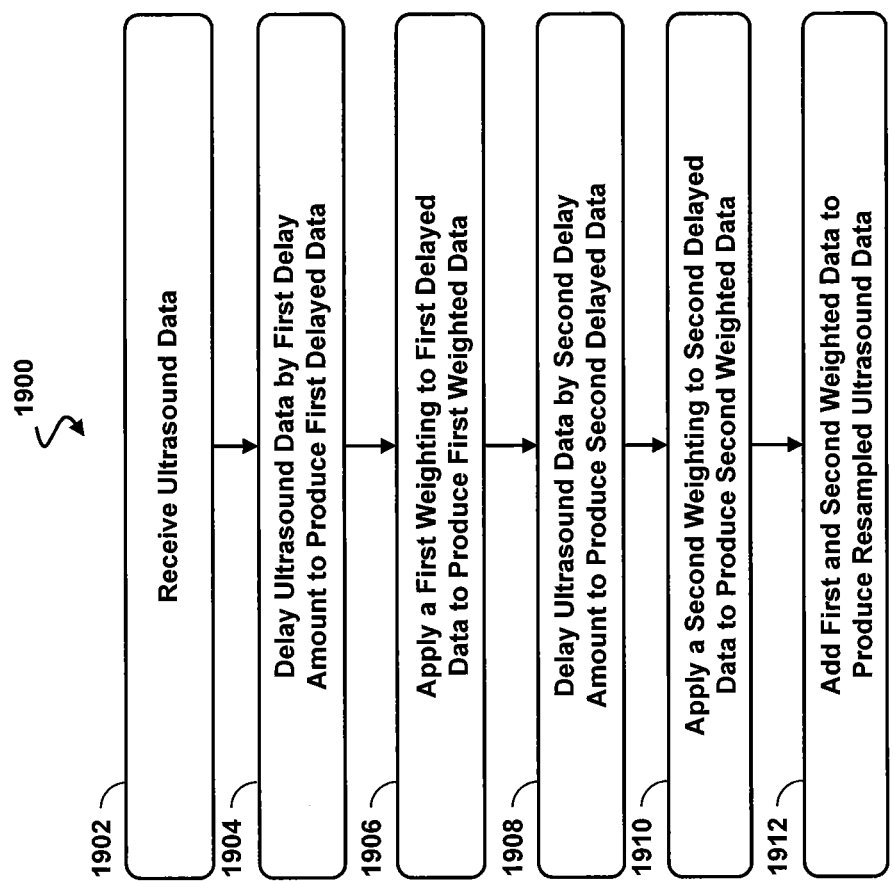
FIG. 19 is a flow diagram of a method of resampling ultrasound data according to aspects of the present disclosure.

FIG. 19 is a flow diagram of a method 1900 of resampling ultrasound data according to aspects of the present disclosure. It is understood that additional steps can be provided before, during, and after the steps of method 1900, and some of the steps described can be replaced or eliminated for other embodiments of the method 1900. Referring to block 1902, an ultrasound echo data stream is received. The ultrasound echo data stream may correspond to A-line echo data. In block 1904, the ultrasound data is delayed by a first delay amount to produce a first delayed data stream. In block 1906, a first weighting value is applied to the first delayed data stream in order to produce a first weighted data stream. The first weighting value may be part of an interpolation filter. For example, the weighting value may be based on a sinc function. The first weighting value may also contain a phase shift component.

In block 1908, the ultrasound data is delayed by a second delay amount to produce a second delayed data stream. In block 1910, a second weighting value is applied to the second delayed data stream. Similar to the first weighting value, the second value may have a component based on an interpolation filter, and/or a component based on a phase shift. In block 1912, the first and second weighted data are added to produce a resampled ultrasound data stream. In some embodiments, the procedures of blocks 1902 through 1912 are performed multiple times in parallel to produce multiple resampled ultrasound data streams. A resampled data stream may be selected from the multiple streams according to an aspect of the A-line that produced the analog data stream such as a geometry of a transducer complex 110, a characteristic of a transducer, a characteristic of an aperture, and/or other relevant factors. As can be seen, the method delivers increased data granularity without the burden of a higher sampling rate.

Figure 20:
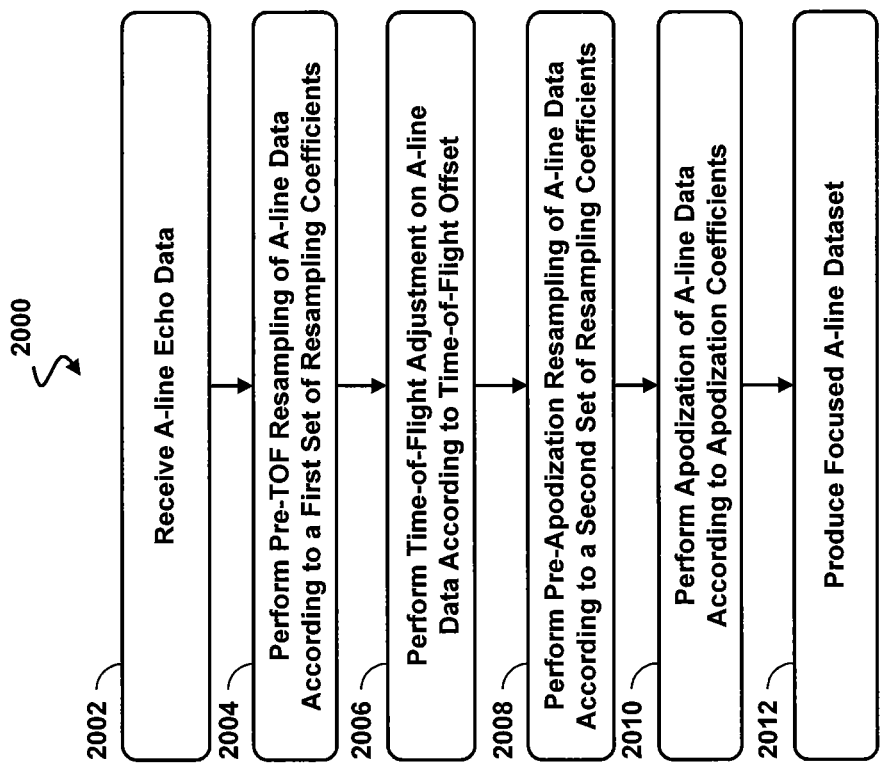
FIG. 20 is a flow diagram of a method of producing focused data utilizing an aperture engine according to aspects of the present disclosure.

FIG. 20 is a flow diagram of a method 2000 of producing focused data utilizing an aperture engine 1300 according to aspects of the present disclosure. It is understood that additional steps can be provided before, during, and after the steps of method 2000, and some of the steps described can be replaced or eliminated for other embodiments of the method 2000. Referring to block 2002, A-line echo data is received. In block 2004, a pre-time-of-flight resampling may be performed according to a first set of resampling coefficients. The resampling coefficients may depend in part on the range and/or flavor of focused A-line data to be calculated, and/or may depend in part on the configuration of the transducer or transducers that produced the A-line data. The resampling coefficients may designate a bump map or may include configuration data from which a bump map can be determined. Accordingly, in some embodiments, pre-time-of-flight resampling includes creating and applying a bump map to produce variable-rate digitized data substantially as disclosed in the method 1000 of FIG. 10. Likewise, in some embodiments, pre-time-of flight resampling includes interpolation and resampling with or without a phase shift substantially as disclosed in the method 1900 of FIG. 19.

In block 2006, a time-of-flight adjustment is performed on the A-line data according to a time-of-flight offset. The time-of-flight offset may correspond to a geometry of a transducer complex, a characteristic of a transducer, a characteristic of an aperture, and/or other relevant factors. The time of flight offset may also correspond to a flavor and/or range to be calculated. In block 2008, a pre-apodization resampling may be performed on the time-of-flight adjusted data according to a second set of resampling coefficients. In various embodiments, the second set of resampling coefficients depend on a geometry of a transducer complex, a characteristic of a transducer, a characteristic of an aperture, a flavor and/or range to be calculated, and/or other relevant factors. In block 2010, apodization is performed on the A-line data according to a set of apodization coefficients. In various embodiments, the apodization coefficients depend on a geometry of a transducer complex, a characteristic of a transducer, a characteristic of an aperture, a flavor or range to be calculated, and/or other relevant factors. In block 2012, focused A-line data is produced in accordance with the aperture assignment.

FIG. 21 is a schematic of a focusing system 2100 according to aspects of the present disclosure. Portions of the focusing system 2100 may be incorporated into an IVUS processing system 106, a patient interface monitor (PIM) 104, and/or other components of an IVUS imaging system 100. The focusing system 2100 includes a number of aperture engines 1300, which perform aperture-processing tasks such as time-of-flight adjustment, amplification, apodization, and summation. Suitable exemplary aperture engines 1300 include the aperture engine 1300 disclosed with reference to FIGS. 13-18. In the illustrated embodiment, the focusing system 2100 includes N aperture engines 1300, of which five are illustrated. In some embodiments, the number of aperture engines 1300 included in the focusing system 2100 is equivalent to the number of transducers 302 within an aperture 304.

Focusing calculations may be divided according to aperture by allocating apertures to the focusing engines 1300. To do so, the aperture engines 1300 receive an aperture assignment from the engine controller 2102. The aperture assignment designates the aperture the engine 1300 is to process and accordingly designates the portion of received A-line data to be used in the focusing calculations. The received A-line data may be received from a transducer complex, a memory subsystem, an analog-to-digital converter, an analog and/or digital amplifier, a filter, a signal conditioner, and/or other suitable interface systems. Once received, the A-line data is placed on an A-line data bus 2104 by which it is distributed to each aperture engine 1300. Only a portion of the received data may be relevant to each aperture and thus each aperture engine 1300. However, in some embodiments, the aperture engines 1300 receive all or substantially all of the A-line data via the data bus 2104. The engines 1300 then pull data off the bus 2104 according to the received aperture assignment. In various embodiments, A-line data that is not part of the assigned aperture may be discarded, may be omitted, may be ignored, may have a zero value coefficient applied, and/or may undergo another culling process. One advantage to this architecture is that data selection at the engines 1300 avoids the need for complicated data steering or filtering circuitry on the bus 2104. In addition to potential wiring, layout, and power benefits, omitting routing and steering circuitry allows for more flexible implementation. For example, in various embodiments, an aperture engine 1300, multiple aperture engines 1300, and/or an entire focusing system 2100 is implemented on a single discrete computing hardware device such as a general purpose processor, a graphic processing unit, an ASIC, an FPGA, a DSP, a microcontroller, or other suitable computing device.

In addition to an aperture assignment, the engine controller 2102 may also provide the aperture engines 1300 with resample coefficients, TOF adjustments, apodization coefficients, and other parameters used to process the A-line data. In some embodiments, the engine controller 2102 includes a set of transducer configurations used to produce bump maps. The engine controller 2102 may also include the bump maps themselves. In some embodiments, the engine controller 2102 includes an apodization coefficient table containing apodization coefficients cross-referenced by emitter/transducer pair. In some embodiments, the engine controller 2102 includes a time-of-flight offset table containing time-of-flight offsets cross-referenced by emitter/transducer pair. In some embodiments, the engine controller 2102 includes a set of resampling rates. These provided parameters including the apodization coefficients within the apodization coefficient table, the time-of-flight offsets within the table, and the resampling rates may be determined based on a geometry of the transducer complex 110, a characteristic of a transducer, a characteristic of an aperture, and/or other relevant factors that affect time-of-flight. The resampling rates may also be determined based on a ratio of samples per pixel of a display unit. One exemplary ratio is 1:1, although other ratios are contemplated and provided for.

As can be seen, the architecture of the focusing system 2100 enables the system 2100 to process multiple apertures in parallel. The aperture engines 1300 process A-line data as it arrives, and after any aperture engine 1300 receives the full A-line dataset for the assigned aperture, the engine 1300 may output the focused A-line data for that aperture. The aperture engine 1300 may then be flushed and begin collecting and processing A-line data for another aperture. This round-robin assignment of apertures to engines 1300 provides high utilization (in some embodiments, full utilization of the engines) without wasted idle resources.

FIG. 22 is a flow diagram of a method 2200 for focusing multiple apertures according to aspects of the present disclosure. It is understood that additional steps can be provided before, during, and after the steps of method 2200, and some of the steps described can be replaced or eliminated for other embodiments of the method. The method 2200 is suitable for implementation using systems such as the focusing system 2100 disclosed with respect to FIG. 21.

In block 2202, a set of apertures 304 are assigned to a set of aperture engines 1300. In some embodiments, the number of apertures within the set of apertures corresponds to the number of engines with the set of engines, which further corresponds to the number of transducers 302 in each of the apertures 304. For example, in an embodiment incorporating nine-transducer apertures, nine adjacent apertures are assigned to nine aperture engines 1300. In the example, aperture 1 is assigned to aperture engine 1, aperture 2 is assigned to aperture engine 2, and so on. In block 2204, an ultrasonic dataset for a transducer 302 within one or more of the apertures is provided to the aperture engines 1300. The dataset may be obtained from the receiving transducer directly, or may be obtained through an intermediary such as a memory subsystem, an analog-to-digital converter, an analog and/or digital amplifier, a filter, a signal conditioner, and/or other suitable interface systems. The ultrasonic dataset is provided to the aperture engines 1300 even though it may not be relevant to the assigned aperture. Continuing the example, a first dataset corresponding to all the receive combinations of a first emitting transducer happens to be relevant to aperture 1 only. For reference, referring back to FIG. 5, the exemplary first emitting transducer is analogous to transducer $T_A$, which is part of aperture 502a. In block 2206 of FIG. 22, it is determined whether any of the aperture engines 1300 has sufficient data to produce a focused A-line dataset. In the example, on the first pass, none of the engines has sufficient data to produce a focused A-line dataset. Thus, the method 2200 returns to block 2204 where another ultrasonic dataset is provided. In the example, a second ultrasonic dataset is relevant to apertures 1 and 2. For reference, the exemplary second emitting transducer is analogous to transducer $T_B$ of FIG. 5, which is part of apertures 502a and 502b. At this point, neither aperture has sufficient data to produce a focused A-line dataset.

In the example, the process repeats until the ninth iteration. On the ninth iteration, exemplary aperture engine 1 has sufficient data to produce a focused A-line dataset, exemplary aperture engine 2 has data for eight of nine emitting transducers, aperture engine 3 has data for seven of nine transducers, and so on. In block 2208, the aperture engine having sufficient data produces the focused A-line dataset. In block 2210, the aperture engine having produced the focused A-line dataset is cleared of stored data. In block 2212, the cleared aperture engine is assigned a next aperture. In the example, aperture engine 1 is assigned aperture 10. The method returns to block 2204 where another ultrasonic dataset is provided. Continuing the example, aperture engine 2 now has sufficient data to produce a focused A-line dataset for aperture 2. Accordingly, aperture engine 2 produces the focused A-line dataset, is flushed, and is assigned aperture 11. This round-robin assignment of apertures allows high utilization of the available aperture engines 1300.

Structural focusing as described above combines A-lines from different spatial angles and positions. Due to these angles and spatial differences, time-of-flight adjustment may be performed in order to align the samples in time. Subsequently the A-lines may be weighted according to their directivity angles and summed. The weighted summing can be understood as a filter operation. In this way, weighting is done on a per sample or per zone basis and while the weighting coefficients change with A-line.

In addition to structural focusing, ultrasound focusing systems may have the ability to detect motion. One method of determining motion in the imaged area is power flow. An example of a power flow algorithm is ChromaFlo® (a trademark of Volcano Corporation). In contrast to focusing spatial A-line data to determine reflection strength of a scatterer, a power flow algorithm may focus temporal A-line data to determine flow rate and spectral intensity of the scatterer. In other words, instead of focusing multiple A-lines within an aperture, a single A-line is fired and captured multiple times. The change in the signal of the A-line between firings can be correlated to scatterer motion. It should be noted that, in many embodiments, the A-line used for power flow imaging contains more than one emitting transducer and more than one receiving transducer. The emitters and receivers operate concurrently, which may improve the signal-to-noise ratio.

To determine changes in time over the series of A-line firings, the data may be weighted and summed. The weighting coefficients may have a range component as well as a temporal component. For example, the weightings applied may comprise a matched filter keyed to an expected rate of change, such as a typical blood velocity. This has the effect of highlighting motion typical of blood flow and deemphasizing other motion common in a biological environment. In the example, the output amplitude of the filter correlates to the flow rate and the scatterer strength. Provided the scatterers are of similar strength, the output of the filter is proportional to the rate change or velocity, and, for a given vessel cross-sectional area, a flow volume may be derived. In addition to deriving flow volume, the weighted data is useful in establishing normal flow patterns as well as vessel flows from plaque burden, stent malapposition. These issues may prove critical to patient health.

The power flow weighted and summing process is directly analogous to the apodization and running sum performed by an aperture engine operating in a spatial mode, for example engine 1300 of focusing system 2100. As, the aperture engines are not limited to focusing spatial series, in some embodiments, the engine controller 2102 of focusing system 2100 is configured to operate one or more of the aperture engines 1300 in a power flow mode. In some embodiments, because the time series of A-lines do not require a time-of-flight adjustment, the time-of-flight adjustment unit of the aperture engine or engines 1300 is bypassed in this mode. Embodiments having a focusing system 2100 that supports both spatial and temporal focusing may add functionality without a significant increase in computing resources. In this way, the flexibility of the aperture engines 1300 may be leveraged to provide added functionality without added cost.

Figure 23:
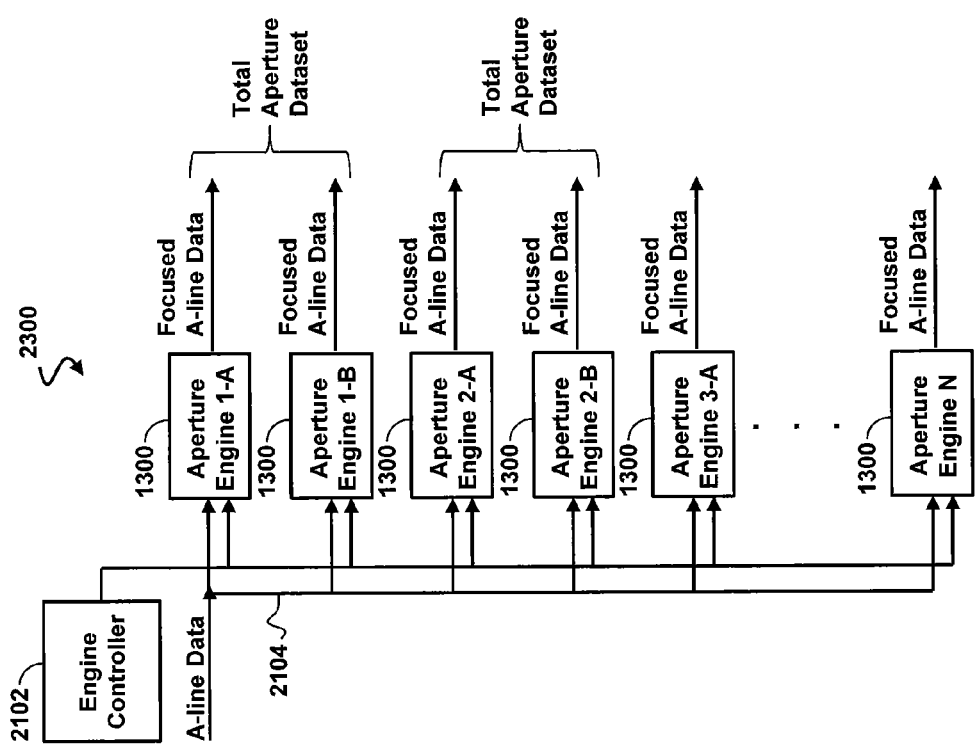
FIG. 23 is a schematic of a focusing system according to aspects of the present disclosure.

FIG. 23 is a schematic of a focusing system 2300 according to aspects of the present disclosure. Portions of the focusing system 2300 may be incorporated into an IVUS processing system 106, a patient interface monitor (PIM) 104, and/or other components of an IVUS imaging system 100. Except as noted, the focusing system 2300 is substantially similar to the focusing system 2100 disclosed with reference to FIG. 21. Whereas in some embodiments, it may prove beneficial to assign one aperture 304 to each aperture engine 1300, other embodiments benefit from alternate configurations. For example, an aperture may be divided by focusing range or A-line flavor across multiple aperture engines. In the illustrated embodiment, focusing system 2300 includes aperture engines 1300 are grouped into pairs (e.g., aperture engine 1-A and engine 1-B), although groups of any magnitude are contemplated. The focusing system 2300 may include a number of groups equivalent to the number of transducers within an aperture. Together, the aperture engines 1300 of a group may produce a complete focused A-line dataset for an aperture 304. Accordingly, each aperture engine 1300 produces a portion of the total data. The processing may be apportioned between the aperture engines 1300 within the group by any suitable division. In some embodiments, each aperture engine 1300 produces data corresponding to a subset of the total flavors in the complete focused A-line dataset. In some embodiments, each aperture engine 1300 produces data corresponding to a subset of the total ranges 1104 in the complete focused A-line dataset. In some embodiments, each aperture engine 1300 produces data corresponding to a subset of the total flavors and ranges in the complete focused A-line dataset.

Accordingly, the engine controller 2102 assigns at least portion of an aperture to each of the aperture engines 1300. The aperture engines 2102 use the aperture assignment to identify and process the relevant data from the A-line data bus 2104. In addition to an aperture assignment, the engine controller 2102 may also provide the aperture engines 1300 with resample coefficients, TOF adjustments, apodization coefficients, and other parameters used to process the A-line data.

This division of the apertures provides various benefits in various embodiments. In some embodiments, aperture engines 1300 configured to process a subset of a focusing engine are physically smaller than in designs where the aperture engines 1300 are configured to produce a full focused dataset. The smaller aperture engines may be implemented on smaller, less powerful circuit devices. This may lead to cost reduction and power savings. In one such embodiment, aperture engines 1300 can be implemented on a small, low cost, and energy efficient FPGA (field programmable gate array). In some embodiments, the smaller aperture engines 1300 can be located nearer to respective inputs and outputs thereby improving system performance. In some embodiments, the smaller aperture engines 1300 can be contained within the IVUS device 102, such as within the transducer complex 110 or within the transmission line bundle 112. This may be referred to as processing "on the wire."

Figure 24:
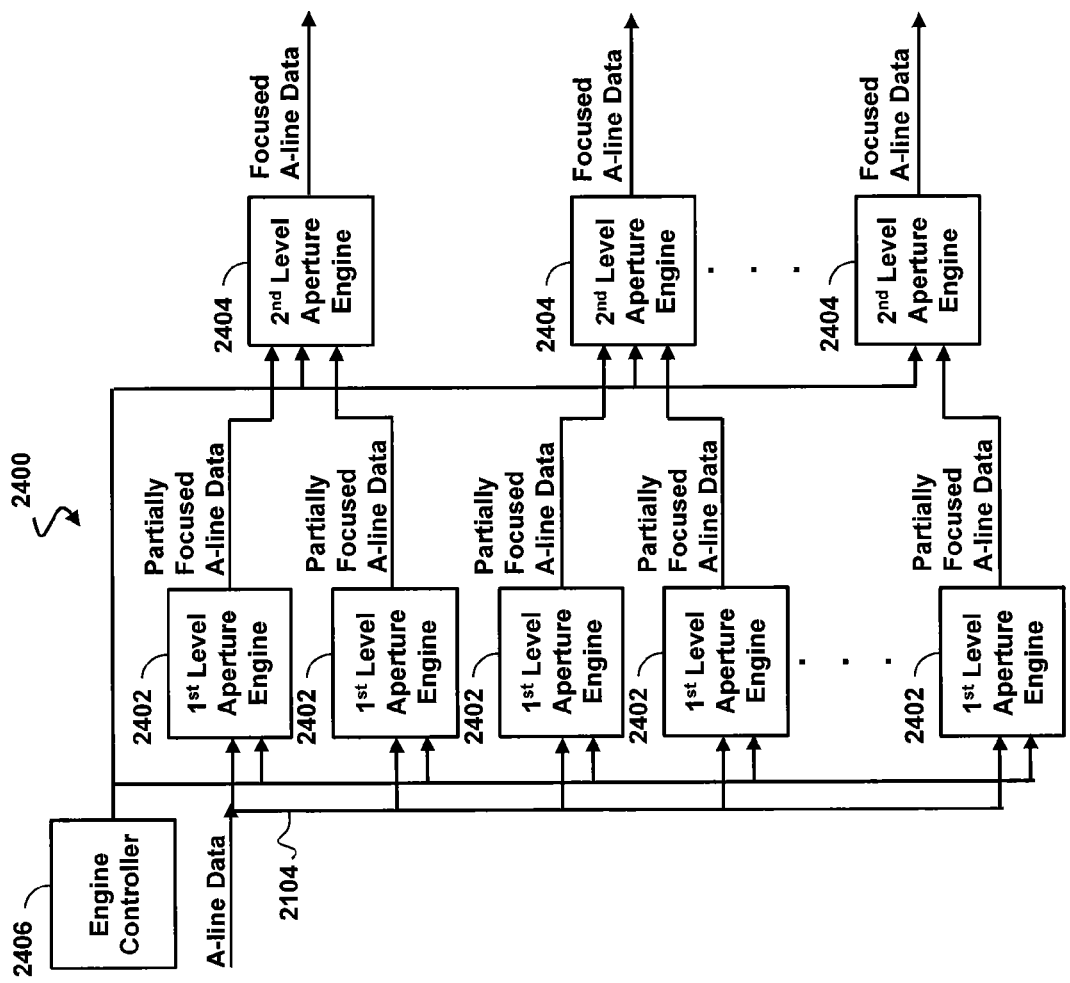
FIG. 24 is a schematic of a hierarchically arranged focusing system according to aspects of the present disclosure.

FIG. 24 is a schematic of a hierarchically arranged focusing system 2400 according to aspects of the present disclosure. Excepted as noted, the focusing system 2400 is substantially similar to the focusing systems disclosed with respect to FIGS. 21 and 23. The focusing system 2400 incorporates one or more hierarchical levels of aperture engines, of which two hierarchical levels are illustrated (designated by first-level engines 2402 and second-level engines 2404). Further embodiments utilize other numbers of hierarchical aperture engines, including 3, 4, and 8, as well as other numbers of levels. A-line data is supplied to the first-level aperture engines 2402. The engine controller 2406, which may be substantially similar to the engine controller 2102 of FIG. 21, may assign sub-apertures (subsets of A-lines within an aperture) to the first-level aperture engines 2402. Sub-apertures may be referred to as co-arrays here and elsewhere. Various divisions of apertures into sub-apertures are contemplated. For example, an aperture may be divided by emitting transducer, receiving transducer, and/or other suitable identifiers. Apertures may be further divided between first-level engines 2402 by focal range and/or A-line flavor. Furthermore, the first-level engines may only be assigned a subset of focusing processes such as interpolation, decimation, resampling, time-of-flight adjustment, apodization, summation, and/or other focusing processes. In an exemplary embodiment, a first-level aperture engine is assigned to perform time-of-flight adjustment but not apodization on a subset of the focal ranges within a sub-aperture. Other divisions are contemplated and provided for.

The first-level aperture engines 2402 perform the assigned focusing tasks according to the sub-aperture assignment substantially as an aperture engine 1300 performs assigned focusing tasks according to an aperture assignment. The first-level aperture engines 2402 may then provide the partially focused data to the second-level aperture engines 2404. The second-level aperture engines 2404 may perform further focusing processes including interpolation, decimation, resampling, time-of-flight adjustment, apodization, summation, and/or other focusing processes. In some embodiments, the second level engines receive an aperture assignment from the engine controller 2406, and the second-level focusing processes are performed accordingly. The partially focused data propagates through the hierarchical levels of aperture engines until it reaches the final hierarchical level of the focusing system 2400 (in the illustrated embodiment, the second level of aperture engines 2404). The aperture engines of the final hierarchical level generate the complete focused A-line dataset for an aperture.

Because, in part, of the division of processing responsibilities among the hierarchical levels, the aperture engines of one hierarchical level (for example, engines 2402) may be identical, similar, or different from the engines of another level (for example, engines 2404). In some embodiments, all the aperture engines of the focusing system 2400 are aperture engines characteristic of those described with respect to FIGS. 13-18. This provides uniformity and simplicity in implementation. In further embodiments, particularly those where aperture engines perform a subset of focusing processes, aperture engines only include the relevant circuitry and thus vary in structure between levels. For example, first-level aperture engines may condition data by applying a filter to enhance the signal to noise-ratio. Such filters may include bandpass filters, matched filters keyed to the excitation pulse, and other filters known to those of skill in the art. If this conditioning does not need to be repeated in subsequent-level aperture engines, the circuitry may be omitted, saving power and circuit area. This specialization may allow engines to be implemented on smaller, more efficient, more economical computing devices, and may allow aperture engines to be combined on a single device. The structure of the focusing system 2400 leverages the parallel processing advantages of the aperture engines while making accommodations for physical, algorithmic, and other limitations that may constrain the functionality of any one aperture engine.

For example, in some embodiments, the device selected to implement an aperture engine may not possess the computing resources to focus a full aperture. Dividing the focusing tasks according to sub-apertures allows data and processing to be apportioned and distributed more effectively. In some embodiments, performance is improved by grouping circuitry near shared resources such as a database of time-of-flight adjustments. Thus, in some embodiments, some aperture engines contain only time-of-flight circuitry and are grouped accordingly. Other engines may have other circuitry for performing other tasks such as apodization and may be grouped accordingly as well.

In some embodiments, levels of aperture engines, such as the first-level aperture engines 2402, are physically remote from those of other levels, such as the second-level aperture engines 2404. These embodiments take a variety of forms. In one such embodiment, the first-level aperture engines 2402 are located within the IVUS device 102, such as within the transducer complex 110 or within the transmission line bundle 112. This may be referred to as processing "on the wire." On the wire processing may simplify the interface between the IVUS device 102 and the rest of the IVUS system 100. On the wire processing may also digitize A-line data signals closer to the transducer complex 110, thereby reducing line loss and transmission noise. In some physically separated embodiments, the first-level aperture engines 2402 are part of a system located within a sterile field, while the second-level aperture engines 2404 are located outside the sterile field, such as in an adjacent observation area. This may reduce the number of wires that cross the sterile boundary. In related embodiments where the first and second-level aperture engines communicate over a wireless communication medium, potential avenues for contamination may be further reduced. In some embodiments, the first-level aperture engines 2402 are part of a sterile package. The sterile package may be designed for aseptic manufacturing, capable of undergoing chemical, radiological, thermal, and other modes of sterilization, and/or may be disposable.

Figure 25:
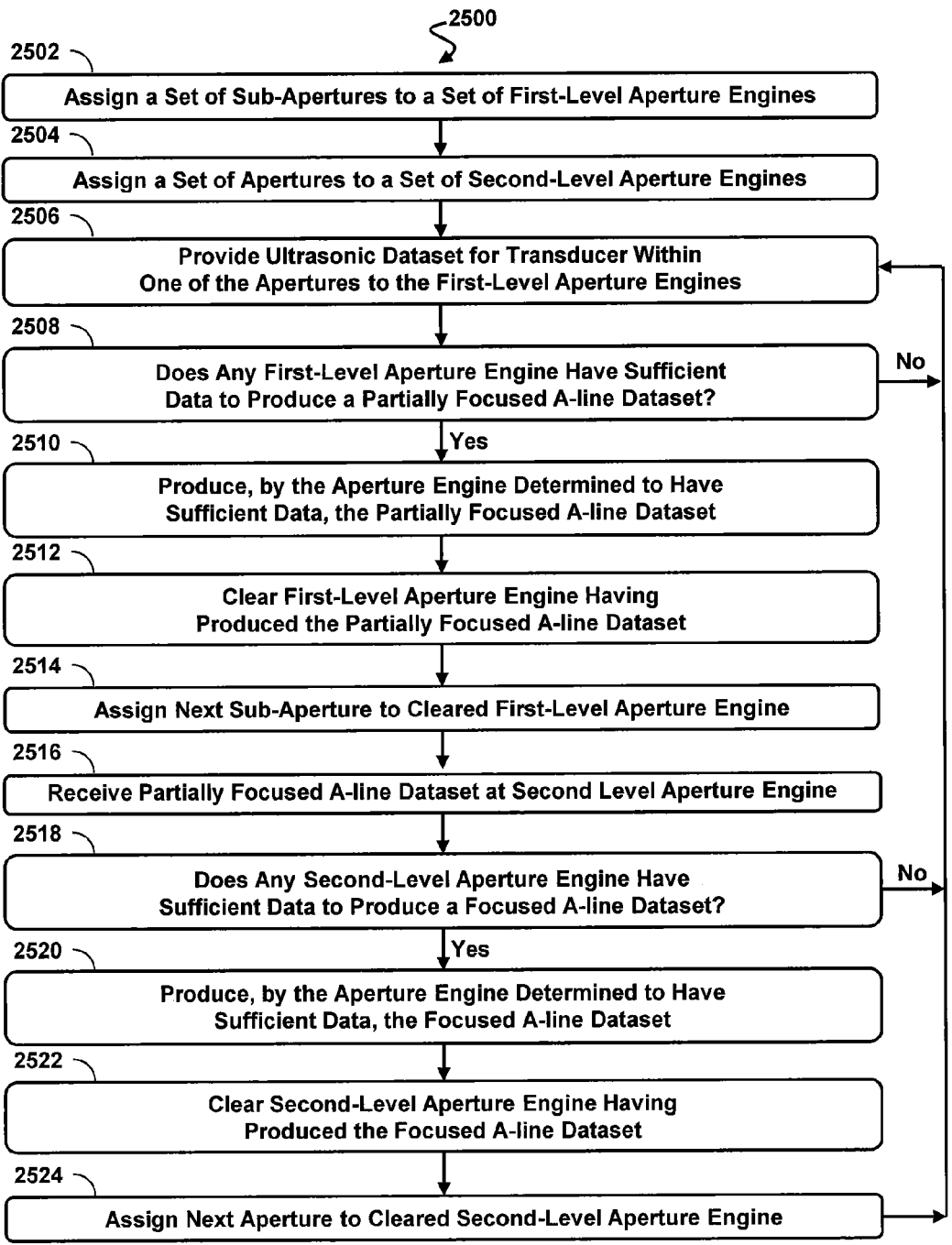
FIG. 25 is a flow diagram of a method for performing hierarchical focusing according to aspects of the present disclosure.

FIG. 25 is a flow diagram of a method 2500 for performing hierarchical focusing according to aspects of the present disclosure. It is understood that additional steps can be provided before, during, and after the steps of method 2500, and some of the steps described can be replaced or eliminated for other embodiments of the method. The method 2500 is suitable for implementation using systems such as the hierarchical focusing system 2400 disclosed with respect to FIG. 24.

In block 2502, a set of sub-apertures are assigned to a set of first-level aperture engines 2402. In an embodiment, the sub-aperture assignment is performed by an engine controller 2406. Each assignment may further divide sub-apertures by subsets of focusing tasks, subsets of focal ranges, subsets of A-line flavors and/or other suitable division criteria. In block 2504, a set of apertures may be assigned to a set of second-level aperture engines 2404. In an embodiment, the aperture assignment is performed by an engine controller 2406. Each aperture assignment may further divide the aperture by subsets of focusing tasks, subsets of focal ranges, subsets of A-line flavors, and/or other suitable division criteria. In an exemplary embodiment, each of nine adjacent nine-transducer apertures is divided into three sub-apertures. Accordingly, three first-level aperture engines are assigned to perform various focusing tasks on one-third of the first aperture (one whole sub-aperture each), three first-level aperture engines are assigned the three sub-apertures of the second aperture, and so on. In block 2506, an ultrasonic dataset for a transducer 302 within one or more of the apertures is provided to the aperture engines 2402. In block 2508, it is determined whether any of the first-level aperture engines 2402 has sufficient data to produce a partially focused A-line dataset. This determination may be made by analyzing each first-level engine 2402 individually and/or by a group analysis. Group analysis may include determining whether other first-level engines assigned a related focusing task have sufficient data to produce a partially focused A-line dataset. For example, the production of data may be synchronized among the sub-apertures within an aperture. In one such embodiment, the determination of block 2508 does not allow the method to proceed to block 2510 until each of the engines assigned a sub-aperture within the aperture has sufficient data to produce a partially focused A-line dataset.

If the engines 2402 do not have sufficient data to produce a focused A-line dataset, the method 2500 returns to block 2506 where another ultrasonic dataset is provided. Once one or more engines 2402 have sufficient data to produce the assigned portion of a focused A-line dataset, the method proceeds to block 2510, where the first-level aperture engine or engines 2402 having sufficient data produce the respective dataset. In block 2512, the first-level engine 2402 that produced the data is cleared of stored A-line data. In block 2514, the cleared first-level engine is assigned the next sub-aperture by the engine controller 2406.

In block 2516 the partially focused A-line dataset is received by a second-level aperture engine 2404. In block 2518, it is determined whether any second level aperture engines 2404 have sufficient data to produce a focused A-line dataset. If not, the method proceeds to block 2506, where additional A-line data is received. On the other hand, if a second-level aperture engine 2404 has sufficient data to produce the respective assigned dataset, in block 2520, the aforementioned focused data is produced. In block 2522, the second-level aperture engine 2404 having produced the dataset is cleared of stored partially focused data. In block 2522, the next sub-aperture may be assigned to the cleared second-level aperture engine 2404 by an engine controller 2406. The method returns to block 2506 where another ultrasonic dataset is provided.

Thus far, embodiments have been described in the context of RF-mode data handling. However, the principles of the disclosure apply equally well to baseband data handling embodiments. Put succinctly, baseband data handling downmixes a high-frequency signal such as A-line echo data to produce a set of complex lower-frequency signals. Because the resulting signals have lower characteristic frequencies, digital sampling rates can be reduced.

Transducers 302 emit an acoustic pulse with a characteristic center frequency f. In ultrasound applications, exemplary center frequencies typically range from 2 MHz to 50 MHz. However, frequencies well beyond this range are contemplated and provided for. The emitted pulse also contains other frequencies within a Gaussian amplitude envelope of fractional bandwidth bw. The reflected pulse produced by a point scatterer and received by a receiving transducer 302 can be approximated by the equation:

$$p(r, t) = Au(\phi_t)u(\phi_r)\cos(\omega t - k(|R_t| + |R_r|))\exp\left(\frac{-(t-\tau)^2}{\sigma^2}\right)$$

where:
$\phi_t$ is the emitter directivity, the angle of incidence between the emitting transducer and the point scatterer,
$\phi_r$ is the receiver directivity, angle of incidence between the point scatterer and the receiving transducer,
A is a constant dependent on the scatter strength and the dispersion of the acoustic wave,
k is the wavenumber, $$\tau = (|R_t| + |R_r|)/V_{sound}$$

$$\sigma = \frac{\log(0.5)}{bw * f} \text{ and}$$

$$u(\phi) = \cos(\phi)\sin\left(\frac{\pi w \sin(\phi)}{\lambda}\right) / \left(\frac{\pi w \sin(\phi)}{\lambda}\right),$$

an exemplary approximation for emissions from a particular transducer.

The pulse is translated into a time varying voltage by the receiving transducer and the resulting signal is mixed with a co-sinusoidal signal ($\cos(\omega t)$) to produce the in-phase signal:

$$I(r,t) \propto p(r,t)\cos(\omega t)$$

The signal is then low-pass filtered to remove the high frequency component. Similarly, by mixing with a sinusoid ($\sin(\omega t)$), the quadrature signal is generated:

$$Q(r,t) \propto p(r,t)\sin(\omega t)$$

This signal is also low-pass filtered. In some embodiments, the two are combined to form a complex amplitude, $D(r,t)$ that includes the complex envelope and the phase of the echo received by the transducer.

$$D(r,t) = I(r,t) + iQ(r,t)$$

In further embodiments, the in-phase and quadrature components are kept as separate channels during the focusing processing. After the focusing is complete, the complex envelope and phase may be derived.

$$Env = \sqrt{I(r;t)^2 + Q(r;t)^2}$$

$$\theta = \tan^{-1}(Q(r;t)/I(r;t))$$

The complex envelope is typically used in structural imaging. The phase may be used in applications such as tissue classification, strain imaging and flow imaging.

The field being imaged can be crudely approximated as an amalgam of point scatterers of varying strength and density distribution. Each scatterer produces an echo and resulting data, which combine linearly. The focusing process measures the scatterer density/strength at a particular point in space by separating out the contributions of scatterers at the point of interest. In a baseband environment, this may be achieved by rotating the phase of the signals recorded by each transmit-receive pairing by multiplying the signals with complex focusing coefficients. Since the phase angle of the complex amplitude signals is largely dependent on the geometry of the echo path (ignoring effects due to inhomogeneous speed of sound, etc.), it is predictable. The phase of the coefficients may be chosen such that echoes from scatterers in the region of interest are phase aligned for each transmit-receive combination. After phase rotation, the signals may be summed. Echoes due to scatterers at the focal point will add coherently while echoes arriving from elsewhere in the medium will not. The resulting signal is a measure of the scatterer density/strength at the focal point.

Figure 26A:
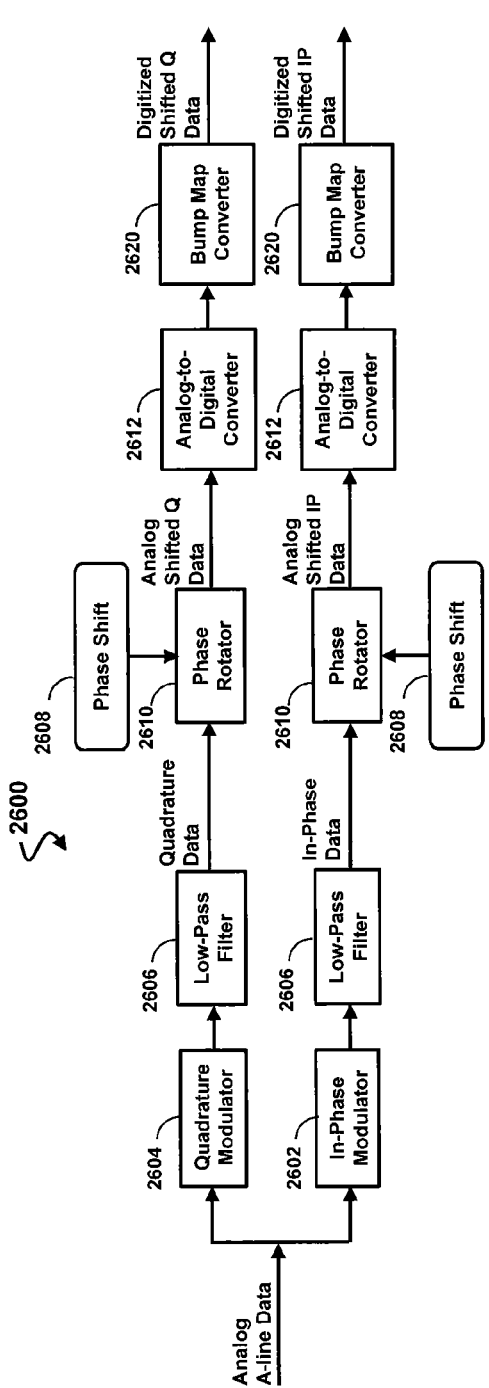
FIGS. 26a and 26b are schematic diagrams of baseband modulators according to aspects of the present disclosure.
Figure 26B:
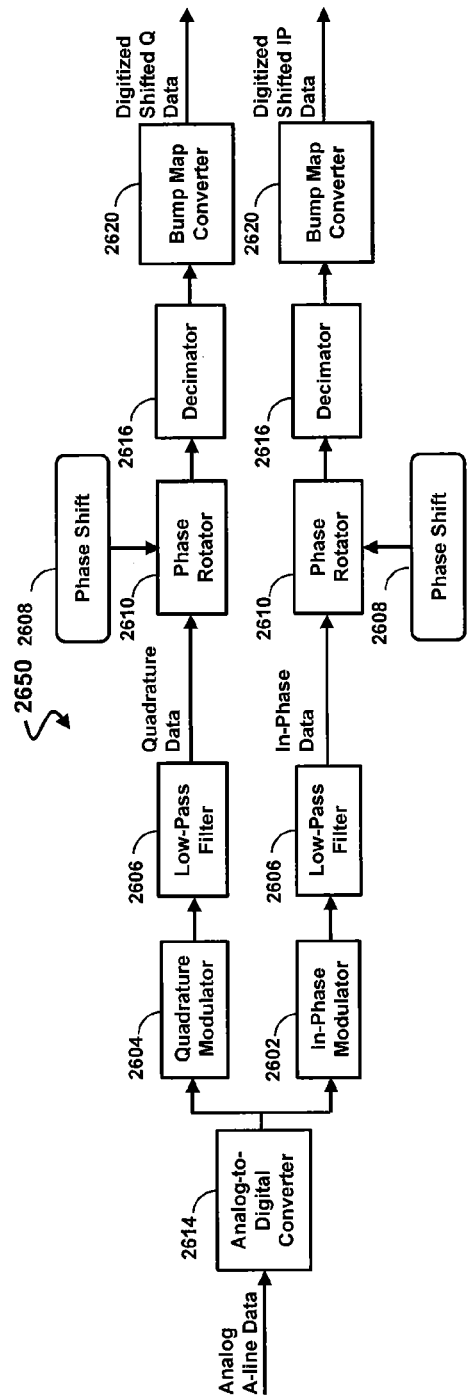

FIGS. 26a and 26b are schematic diagrams of baseband modulators according to aspects of the present disclosure. As can be seen, the baseband conversion can be performed using either digital or analog data signals. Referring first to FIG. 26a, a baseband modulator 2600 receives analog A-line data. The received A-line data may be received from a transducer complex 110, an analog amplifier, a filter, a signal conditioner, and/or other suitable interface systems. The in-phase modulator 2602 mixes the incoming data with a co-sinusoidal signal (cos(ωt)) to produce the in-phase signal. The resulting signal is passed through a low-pass filter 2606. Similarly, the quadrature modulator 2604 mixes the incoming data with a sinusoidal signal (sin(ωt)) to produce the quadrature signal. This signal is also passed through a low-pass filter 2606.

The focusing process attempts to isolate the echo signals created by individual scatterers from the A-line data and thereby measure scatter density at a given location. In the baseband environment, this may be performed by time shifting and aligning the in-phase and quadrature components of the received A-line data. One skilled in the art will recognize the similarities between baseband time shifting and time-of-flight adjustment disclosed in the context of RF embodiments. In baseband embodiments, time shifting may be implemented as two distinct steps. A phase rotator 2610 may be used to shift the analog data by degree increments of less than one sample. For example, a phase shift of 180° may shift the incoming A-line data in time by half of a sampling interval. The phase shift values 2608 used by the phase rotator 2610 may be based on a geometry of the transducer complex 110, a characteristic of a transducer, a characteristic of an aperture, and/or other relevant factors that affect arrival time. Time alignment of greater than one sample may be performed using a bump map, for example, as disclosed with reference FIGS. 9a and 9b. Together, the phase rotator 2610 and the bump map converter 2620 may supplement or replace time-of-flight correction in the RF domain.

In the embodiment of FIG. 26a, analog in-phase and quadrature signals are phase adjusted by the phase rotators 2610 according to the phase shift value 2608, digitized by one or more analog-to-digital converters 2612, and resampled by the bump map converter 2620 to produce digitized baseband A-line data. In various related embodiments, the analog-to-digital converter and the bump map converter 2620 are integrated into a variable-clock-rate digitizer.

In contrast to the embodiments of FIG. 26a, analog-to-digital conversion may be performed earlier in the baseband data flow. FIG. 26b illustrates embodiments where a greater portion of the baseband data handling is performed on digitized data. The baseband modulator 2650 of FIG. 26b is substantially similar to that of baseband modulator 2600 of FIG. 26a, except as noted. In the illustrated embodiment, analog A-line data is received by an analog-to-digital converter 2614 where it is digitized. The received A-line data may be received from a transducer complex 110, an analog amplifier, a filter, a signal conditioner, and/or other suitable interface systems. The digitized A-line data is then provided to digital in-phase 2602 and quadrature modulators 2604. The modulated signals are provide to digital low-pass filters 2606. The filtered signals are rotated by the phase rotators 2610 according to the phase shift values 2608.

In some embodiments, the sampling frequency of the summed signals is reduced by a decimator 2616. This can be performed without significant loss of accuracy because of an advantage to baseband data handling that may be leveraged by embodiments of both FIGS. 26a and 26b. The process of forming the in-phase and quadrature signals downmixes the A-line data stream by the center frequency. The result is a signal with a lower effective frequency. This lower-frequency signal can be digitized using a sampling rate proportional to the half-bandwidth instead of the center frequency plus the half-bandwidth. As the Nyquist rate, the minimum sampling rate needed to avoid aliasing, is twice the highest frequency of interest, the reduction in number of samples may be considerable. The reduced sampling rate may accordingly reduce bus speed, data storage requirements, clock frequency, power consumption, and/or processing hardware required for other focusing steps.

Following decimation, one or more bump map converters 2620 perform further time shifting on the in-phase and quadrature baseband data. It will be recognized that decimation and bump map conversion may be performed as part of a single process. Therefore, in some embodiments, the bump map converters 2620 receive bump maps configured to perform decimation as well as time shifting. In further embodiments, the bump map converters 2620 are integrated into the analog-to-digital converter(s) 2614 positioned earlier in the dataflow. In such embodiments, time adjusting via the bump maps is performed prior to modulation, filtering, and phase shifting. These and other configurations are encompassed within the scope of the disclosure.

Figure 27:
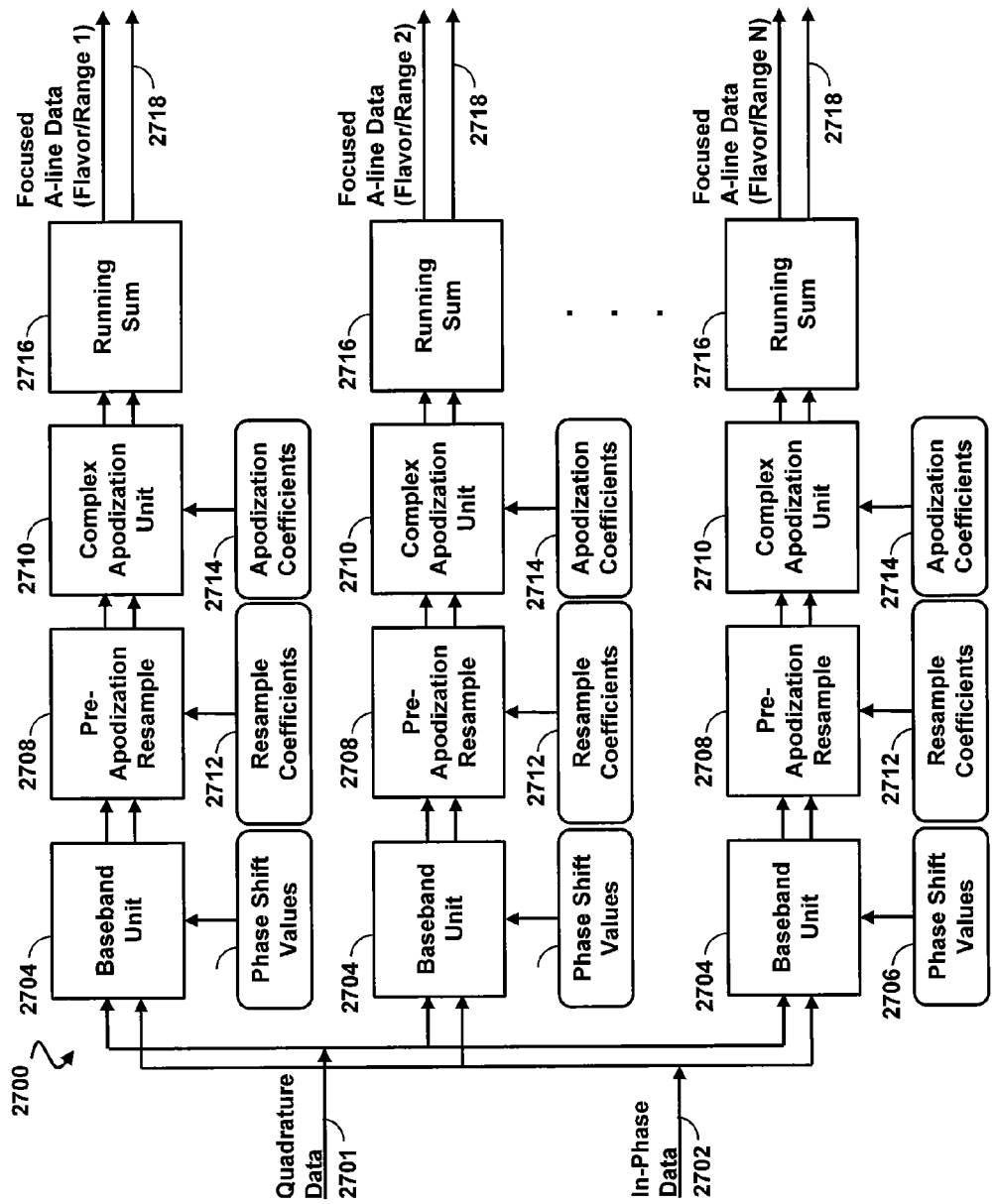
FIG. 27 is a schematic of a baseband aperture engine according to aspects of the present disclosure.

FIG. 27 is a schematic of a baseband aperture engine 2700 according to aspects of the present disclosure. Portions of the baseband aperture engine 2700 may be incorporated into an IVUS processing system 106, a patient interface monitor (PIM) 104, and/or other components of an IVUS imaging system 100. In some embodiments, the baseband aperture engine 2700 provides a parallelizable focusing engine used in an IVUS system 100 to leverage concurrent processing of multiple apertures in order to improve processing throughput. In many aspects, the baseband aperture engine 2700 is substantially similar to the aperture engine 1300 disclosed with respect to FIGS. 13-18.

The baseband aperture engine 2700 receives baseband A-line data, which may include a quadrature data component 2701 and/or an in-phase data component 2702. This data may be received from a transducer complex 110, a memory subsystem, an analog-to-digital converter, an analog and/or digital amplifier, a filter, a signal conditioner, and/or other suitable interface systems. The received A-line data is provided to a baseband unit 2704. Suitable baseband units include those described with respect to FIGS. 23a and 23b. The baseband units 2704 may apply filtering, phase rotation according to received phase shift values 2706, complex summation, analog-to-digital conversion, and/or resampling using a bump map to the received A-line data 2702 as described with respect to FIGS. 23a and 23b.

In embodiments incorporating a pre-apodization resample unit 2708, the baseband A-line data may be supplied in analog and/or digital form, and may be supplied as separate in-phase and quadrature components and/or as a complex sum of the two components. When analog baseband A-line data is provided, the resample unit 2708 may digitize the analog data. Resampling of digital A-line data may also be performed by the resample unit 2708. In this way, the resample unit 2708 of some embodiments may be significantly similar to the pre-apodization resample unit 1404 of FIG. 14. In various embodiments, resampling includes upsampling, such as full upsampling and interpolated phase shifting, and/or downsampling, such as decimation. Resampling algorithms are known to those of skill in the art. Non-limiting examples of resampling algorithms include linear interpolation, Lagrange interpolation, cubic spline interpolation, polyphase interpolation, and/or other suitable algorithms. The pre-apodization resample unit 2708 may resample digital A-line data based on a set of resample coefficients 2712. The resample coefficients 2712 may specify a resampling rate, may specify a resampling algorithm, may supply coefficients for a resampling algorithm, and/or may supply other resampling configuration data. In some embodiments, sampling rates above a certain ceiling do not improve the quality of the final focused image. In such embodiments, the ceiling is determined in part by a resolution or number of pixels in the final image. Accordingly, the pre-apodization unit may reduce the sample frequency of the baseband A-line data by performing a decimation process according to a ratio of samples per pixel. For example, the ratio of samples per pixel may be 1:1.

As disclosed above, reducing the sample frequency may result in a more efficient architecture. In some embodiments, downsampling allows for lower bus speeds, less data buffering, reduced clock frequency, lower memory requirements for data storage, and/or a reduced power envelope. Reduced data handling requirements may also allow more flexible division of hardware among computing devices such as general purpose processors, a graphic processing units, ASICs, FPGAs, a DSPs, and a microcontrollers. These advantages are not limited to improved efficiency in the data pipeline. Reducing the dataset may also reduce the size and complexity of functional circuitry such as the complex apodization unit 2710 providing additional size, power, and cost savings.

The complex apodization unit 2710 receives baseband A-line data from the baseband unit 2704 and/or the pre-apodization resample unit 2708 and, similar to the apodization unit 1208 disclosed with respect to FIG. 12, may perform amplitude balancing and/or apodization functions weighted to reduce effects such as sidelobe effects and grating effects. Apodization functions include boxcar, Hann, Hamming, cosine, half-cosine window function and/or other suitable apodization function. In some embodiments, the complex apodization unit 2710 applies a directional amplitude adjustment, a sensitivity adjustment, and/or other amplitude modifications. These may be specified by one or more apodization coefficients 2714. As the baseband A-line data may be a set of in-phase and quadrature components or a complex sum of the components, the supplied apodization coefficients 2714 may include sets of in-phase and quadrature values and/or may include complex values.

The resulting apodized baseband A-line data is supplied to the running sum unit 2716 where it is added with apodized baseband A-line data for other A-lines within an aperture. When the appropriate data has been processed and summed, the focused A-line data 2718 for the aperture may be produced. The focused A-line data 2718 may be in baseband or RF form, and may be represented as separate in-phase and quadrature components or as a complex sum of the components.

FIG. 28 is a flow diagram of a method 2800 of baseband aperture focusing according to aspects of the present disclosure. It is understood that additional steps can be provided before, during, and after the steps of method 2800, and some of the steps described can be replaced or eliminated for other embodiments of the method 2800. Referring to block 2802, an aperture assignment and A-line data is received. The aperture assignment designates a portion of the received A-line data that is relevant to the assigned aperture. In block 2804, baseband modulation is performed on at least the designated A-line data. Baseband modulation produces in-phase and quadrature components either separately or as a complex sum. In block 2806, phase modulation is performed on the modulated A-line data according to a phase modulation value.

In block 2808, a pre-apodization resampling may be performed on the phase modulated A-line data according to a set of resampling coefficients. In block 2810, complex apodization is performed on the baseband A-line data. In some embodiments that perform pre-apodization resampling, apodization (including apodization and amplitude modulation) is performed on the resampled data produced in block 2808. In alternate embodiments, apodization is performed on the phase modulated baseband data of block 2806. In block 2812, focused A-line data is produced in accordance with the aperture assignment.

FIG. 29 is a schematic of a baseband focusing system 2900 according to aspects of the present disclosure. The focusing system 2900 may be incorporated into an IVUS processing system. The baseband focusing system 2900 is substantially similar to the focusing system 2100 disclosed with reference to FIG. 21. The baseband focusing system 2900 includes a number of baseband aperture engines 2700, which perform aperture-processing tasks such as phase rotation, amplification, apodization, and summation. Suitable exemplary baseband aperture engines 2700 include the engine disclosed with reference to FIG. 27. In the illustrated embodiment, the focusing system 2900 includes N baseband aperture engines 2700, of which five are illustrated. In some embodiments, the number of baseband aperture engines 2700 included in the baseband focusing system 2900 is equivalent to the number of transducers 2700 within an aperture 304. This structure enables the baseband focusing system 2900 to process multiple apertures in parallel.

Focusing calculations may be divided according to aperture by allocating apertures to the focusing engines 2700. To do so, the aperture engines 2700 receive an aperture assignment from the engine controller 2902, which may be substantially similar to engine controller 2102 of FIG. 21. The aperture assignment designates the aperture that the engine 2700 is to process and accordingly designates the portion of received A-line data to be used in the focusing calculations. Received A-line data is placed on an A-line data bus 2104 and distributed to each aperture engine 2700. The received A-line data may be received from a transducer complex 110, a memory subsystem, an analog-to-digital converter, an analog and/or digital amplifier, a filter, a signal conditioner, and/or other suitable interface systems. Only a portion of the received data may be relevant to each aperture and thus each aperture engine 2700. Accordingly, the aperture engines 2700 use the aperture assignment to identify and process the relevant data from the A-line data bus 2104. In various embodiments, A-line data that is not part of the assigned aperture may be discarded, may be omitted, may be ignored, may have a zero value coefficient applied, and/or may undergo another culling process. One advantage to this architecture is that data selection at the engines 2700 avoids the need for complicated data steering or filtering circuitry on the bus 2104. In addition to potential wiring, layout, and power benefits, omitting routing and steering circuitry allows for more flexible implementation. For example, in various embodiments, an aperture engine 2700, multiple aperture engines 2700, and/or an entire focusing system 2900 is implemented on a single discrete computing hardware device such as a general purpose processor, a graphic processing unit, an ASIC, an FPGA, a DSP, a microcontroller, or other suitable computing device.

In addition to an aperture assignment, the engine controller 2902 may also provide the aperture engines 2700 with resample coefficients, phase shift values, apodization coefficients, and other parameters used to process the A-line data. Once any aperture engine 2700 receives the A-line dataset for the assigned aperture, the engine 2700 produces the focused A-line data for that aperture. The aperture engine 2700 may then be flushed and begin collecting and processing A-line data for another aperture. This round-robin assignment of apertures to engines 2700 provides high utilization without wasted idle resources.

FIG. 30 is a flow diagram of a method 3000 for focusing multiple apertures according to aspects of the present disclosure. It is understood that additional steps can be provided before, during, and after the steps of method 3000, and some of the steps described can be replaced or eliminated for other embodiments of the method. The method 300 is suitable for implementation using systems such as the baseband focusing system 2900 disclosed with respect to FIG. 29.

In block 3002, a set of apertures 304 are assigned to a set of baseband aperture engines 2700. In some embodiments, the assignment is performed by an engine controller 2902. In some embodiments, the number of apertures within the set of apertures corresponds to the number of engines with the set of engines, which further corresponds to the number of transducers 302 in each of the apertures 304. In block 3004, an ultrasonic dataset for a transducer 302 within one or more of the apertures is provided to the baseband aperture engines 3006. The dataset may be obtained from the echo data directly, or may be obtained through an intermediary such as a memory subsystem, an analog-to-digital converter, an analog and/or digital amplifier, a filter, a signal conditioner, and/or other suitable interface systems. The ultrasonic dataset may be provided to the baseband aperture engines 2700 even though it may not be relevant to the assigned aperture.

In block 3006, it is determined whether any of the aperture engines 2700 has sufficient data to produce a focused A-line dataset. In block 3008, the aperture engine having sufficient data produces the focused A-line dataset. In block 3010, the aperture engine having produced the focused A-line dataset is cleared of stored data. In block 3012, the cleared aperture engine is assigned a next aperture. The method returns to block 3004 where another ultrasonic dataset is provided.

Figure 31:
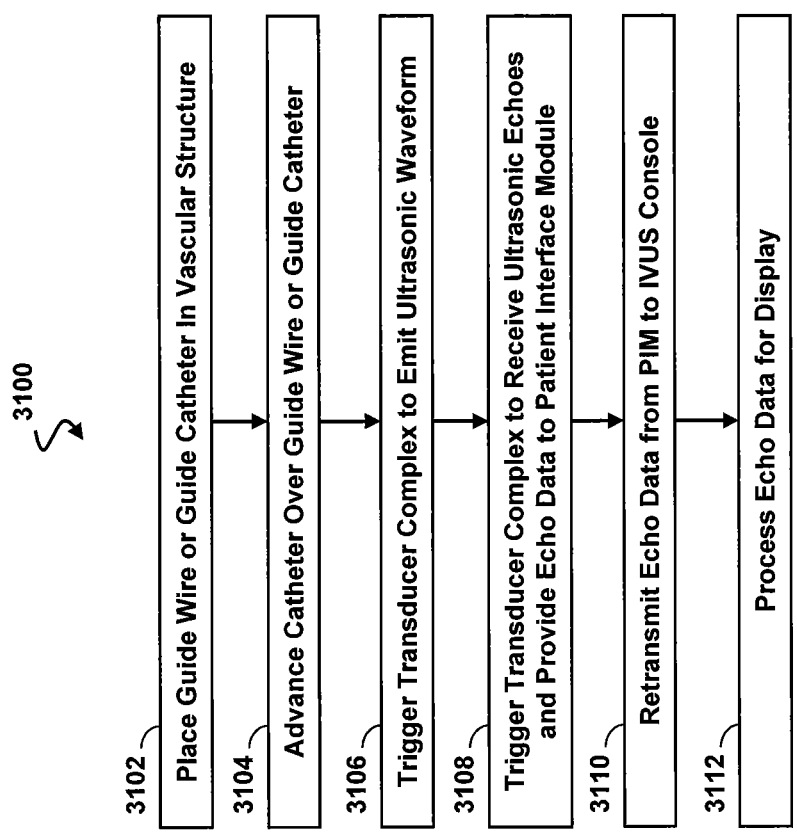
FIG. 31 is a flow diagram of a method of utilizing the IVUS device according to aspects of the present disclosure.

A method 3100 of utilizing an IVUS device 102 is disclosed referring to FIG. 31 and referring back to FIG. 1. FIG. 31 is a flow diagram of the method of utilizing the IVUS device 102 according to an embodiment of the present disclosure. It is understood that additional steps can be provided before, during, and after the steps of method 3100, and some of the steps described can be replaced or eliminated for other embodiments of the method.

Referring to block 3102 of FIG. 31 and to FIG. 1, in an illustrative example of a typical environment and application of the system, a surgeon places a guide wire 118 in the vascular structure 120. The guide wire 118 is threaded through at least a portion of the distal end of the IVUS device 102 either before, during, or after placement of the guide wire 118. Referring to block 3104 of FIG. 31, once the guide wire 118 is in place, the IVUS device 102 is advanced over the guide wire. Referring to block 3106, the transducer complex 110 is activated. Signals sent from the PIM 104 to the transducer complex 110 via the transmission line bundle 112 cause transducers within the complex 110 to emit a specified ultrasonic waveform. The ultrasonic waveform is reflected by the vascular structure 120. Referring to block 3108 of FIG. 31, the reflections are received by the transducers within the complex 110 and are amplified for transmission via the transmission line bundle 112. The echo data is placed on the transmission line bundle 112 and sent to the PIM 104. The PIM 104 amplifies the echo data and/or performs preliminary pre-processing, in some instances. Referring to block 3110 of FIG. 31, the PIM 104 retransmits the echo data to the IVUS console 106. Referring to block 3112 of FIG. 31, the IVUS console 106 aggregates and assembles the received echo data to create an image of the vascular structure 120 for display on the monitor 108. In some exemplary applications, the IVUS device is advanced beyond the area of the vascular structure 120 to be imaged and pulled back as the transducer complex 110 is operating, thereby exposing and imaging a longitudinal portion of the vascular structure 120. To ensure a constant velocity, a pullback mechanism is used in some instances. A typical withdraw velocity is 0.5 mm/s, although other rates are possible based on beam geometry, sample speed, and the processing power of the system. In some embodiments, the device 102 includes an inflatable balloon portion 122. As part of a treatment procedure, the device may be positioned adjacent to a stenosis (narrow segment) or an obstructing plaque within the vascular structure 120 and inflated in an attempt to widen the restricted area of the vascular structure 120.

Persons skilled in the art will recognize that the apparatus, systems, and methods described above can be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

While the present disclosure is directed primarily to ultrasonic imaging, the system disclosed herein is well suited to focusing any type of phased array data. This includes data produced and collected by ultrasound transducers, radio-frequency transducers, and x-ray transducers. Such applications include tomographic imaging (e.g., CT (computed tomography), microCT, PET (positron emission tomography), and microPET). Beyond medical imaging, focusing may take place in cellular communications, satellite communications, satellite imaging, radar LADAR, and other technologies. One skilled in the art will recognize the application of the principles herein across these and other disciplines.

What is claimed is:

1. An ultrasound imaging system, comprising:
    an intravascular imaging device sized and shaped for insertion into a vessel; and
    a processing system in communication with the intravascular imaging device, the processing system comprising:
        first and second aperture engines;
        an A-line data interface providing at least a portion of A-line data to the first and second aperture engines; and
        an engine controller communicatively coupled to the first and second aperture engines;
        wherein the engine controller provides at least first and second aperture assignments designating portions of the A-line data to the first and second aperture engines, respectively;
        wherein the first and second aperture engines:
            receive the first and second aperture assignments, respectively;
            receive the at least a portion of the A-line data;
            perform one or more focusing processes on the received A-line data; and
            produce focused data in accordance with the first and second aperture assignments, respectively.

2. An ultrasound imaging system, comprising:
    a processing system in communication with an ultrasound imaging device, the processing system comprising:
        a first aperture engine configured to receive first imaging data obtained by a first plurality of imaging elements associated with a first aperture of the ultrasound imaging device;
        a second aperture engine configured to receive second imaging data obtained by a second plurality of imaging elements associated with a second aperture of the ultrasound imaging device;
        wherein the first and second aperture engines are configured to concurrently perform one or more focusing processes on the received first and second imaging data respectively.

3. The ultrasound imaging system of claim 2, wherein the first aperture engine is cleared of the first imaging data when it is determined that the first aperture engine has performed the one or more focusing processes on the first imaging data, and wherein the first aperture engine is configured to receive third imaging data obtained by a third plurality of imaging elements associated with a third aperture of the ultrasound imaging device after clearing the first imaging data; and
wherein the second aperture engine is cleared of the second imaging data when it is determined that the second aperture engine has performed the one or more focusing processes on the second imaging data, and wherein the second aperture engine is configured to receive fourth imaging data obtained by a fourth plurality of imaging elements associated with a fourth aperture of the ultrasound imaging device after clearing the second imaging data.

4. The ultrasound imaging system of claim 2,
wherein the first imaging data is associated with a first range of focus; and
wherein the second imaging data is associated with a second range of focus.

5. The ultrasound imaging system of claim 2, further comprising:
the ultrasound imaging device.

6. The ultrasound imaging system of claim 2, wherein the ultrasound imaging device is configured to be inserted into a patient body.

7. The ultrasound imaging system of claim 2, wherein the ultrasound imaging device comprises a catheter or a guidewire.

8. The ultrasound imaging system of claim 2, wherein the first aperture engine comprises:
    a bump map generator configured to generate a bump map based on a configuration of the first plurality of imaging elements;
    a clock signal generator configured to generate a fixed clock frequency; and
    an analog-to-digital converter configured to receive analog data corresponding to the first plurality of imaging elements and to produce digital data based on the analog data being sampled at a sampling rate determined based on the fixed clock frequency and the bump map.

9. The ultrasound imaging system of claim 8, wherein the bump map generator is configured to generate the bump map based on emitter-receiver pairs of first and second plurality of imaging elements.

10. The ultrasound imaging system of claim 2, wherein the first aperture engine is configured to receive the first imaging data from the first plurality of imaging elements according to at least one of a forward or a backward walk pattern through the first plurality of imaging elements.

11. The ultrasound imaging system of claim 2, wherein the first plurality of imaging elements and the second plurality of imaging elements comprise ultrasound transducers configured to transmit and receive imaging signals.

12. The ultrasound imaging system of claim 2, further comprising a third plurality of imaging elements including the first plurality of imaging elements and the second plurality of imaging elements, wherein the third plurality of imaging elements are organized into a plurality of apertures including the first aperture and the second aperture, and wherein one or more imaging elements are included in more than one aperture.

13. The ultrasound imaging system of claim 2,
wherein each of the first and second aperture engines includes a time-of-flight unit; and
wherein the one or more focusing processes includes a time-of-flight adjustment.

* * * * *